US012735454B2

(12) United States Patent
Jiang et al.

(10) Patent No.: US 12,735,454 B2
(45) Date of Patent: Sep. 15, 2026

(54) PEPTIDE COMPOUND TARGETING ELASTIN-DERIVED PEPTIDES AND USE THEREOF

(71) Applicant: Shenzhen Turier Biotech Co., Ltd., Shenzhen (CN)

(72) Inventors: Xianxing Jiang, Shenzhen (CN); Rui Wang, Shenzhen (CN); Nazi Song, Shenzhen (CN)

(73) Assignee: Shenzhen Turier Biotech Co., Ltd. (CN)

( * ) Notice: Subject to any disclaimer, the term of this patent is extended or adjusted under 35 U.S.C. 154(b) by 747 days.

(21) Appl. No.: 18/007,626

(22) PCT Filed: May 19, 2021

(86) PCT No.: PCT/CN2021/094680

§ 371 (c)(1),
(2) Date: Dec. 1, 2022

(87) PCT Pub. No.: WO2021/249143

PCT Pub. Date: Dec. 16, 2021

(65) Prior Publication Data

US 2024/0336653 A1 Oct. 10, 2024

(30) Foreign Application Priority Data

Jun. 8, 2020 (CN) ........................ 202010515052.8

(51) Int. Cl.

| | |
|---|---|
| ***C07K 7/08*** | (2006.01) |
| ***A61K 38/00*** | (2006.01) |
| ***A61P 1/16*** | (2006.01) |
| ***A61P 11/00*** | (2006.01) |
| ***C07K 7/64*** | (2006.01) |

(52) U.S. Cl.
CPC .................. *C07K 7/08* (2013.01); *A61P 1/16* (2018.01); *A61P 11/00* (2018.01); *C07K 7/64* (2013.01); *A61K 38/00* (2013.01)

(58) Field of Classification Search
None
See application file for complete search history.

(56) References Cited

FOREIGN PATENT DOCUMENTS

| | | | | | |
|---|---|---|---|---|---|
| CN | 111704653 | A | | 9/2020 | |
| JP | 2014508147 | A | | 4/2014 | |
| JP | 2002520421 | A | | 7/2022 | |
| WO | 2012156641 | A1 | | 11/2012 | |
| WO | WO-2018141970 | A1 | * | 8/2018 | .......... C07K 14/705 |
| WO | 2021040526 | A1 | | 3/2021 | |

OTHER PUBLICATIONS

Joo (Biomol Ther (Seoul). Jan. 2012;20(1):19-26) (Year: 2012).*
Leslie, Science Now, May 2012 (Year: 2012).*
Panos et al., Am J Med. Apr. 1990;88(4): 396-404 (Year: 1990).*
European Patent Office; Extended European Search Report issued in EP App No. 21821478.1 dated Jun. 5, 2024; 9 pages.
Tan Huanbo et al: "Recent Advances in Half-life Extension Strategies for Therapeutic Peptides and Proteins", Current Pharmaceutical Design, vol. 24, No. 41, Jan. 1, 2018 (Jan. 1, 2018), pp. 4932-4946, XP055868389, NL ISSN: 1381-6128, DOI: 10.2174/1381612825666190206105232 Retrieved from the Internet: U RL: https ://eurekaselect.com/article/download/1 69638.
Korean Patent Office; First Office Action issued in corresponding KR Patent App. No. 10-2023-7000148 dated Jun. 17, 2025, 8 pages.
Chow , Hoi Yee , et al. Ligation Technologies for the Synthesis of Cyclic Peptides. Chemical Reviews , 2019 , 119(17):9971-10001.
D. C. Rockey et al.; "Fibrosis—A Common Pathway to OrganInjury and Failure"; The New England Journal of Medicine; doi:10:1056/NEJMra1300575; Mar. 19, 2015, 372;12; pp. 1138-1149.
L. Petitclerc et al.; "Liver Fibrosis: Review of Current Imaging and MRI Quantification Techniques"; Journal of Magnetic Resonance Imaging; doi: 10/1002/jmro.25550; JMRI2017; 45; pp. 1276-1295.
K. Bottcher et al.; "Pathophysiology of liver fibrosis and the methodological barriers to the development of anti-fibrogenic agents"; Advanced drug delivery reviews; doi: 10.1016/j.addr.2017.05.016; Jun. 9, 2017; 121, 3-8; 6 pages.
A. H. Ali et al.; "Obeticholic acid for the treatment of primary billiary cholangitis"; Expert opinion on pharmacotherapy; doi: 10.1080/14656566.2016.1218471; Jul. 28, 2016; 17; 1809-1815.
L. Richeldi et al.; "Idiopathic pulmonary fibrosis"; The Lancet; doi: 10/1016/S0140-6736(17)30866-8; Mar. 29, 2017, 389, 1941-1952.
D. J. Lederer et al.; "Idiopathic Pulmonary Fibrosis"; The New England Journal of Medicine; doi: 10.1056/NEJMra1705751; May 10, 2018; 378; 1811-1823.
K. F. Rabe et al.; "Chronic obstructive pulmonary disease"; The Lancet; May 13, 2017, vol. 389, 1931-1940.
Robert M. Senior et al.; "Chemotactic responses of fibroblasts to tropoelastin and elastin-derived peptides"; J. Clin. Invest.; Sep. 1982; vol. 70, pp. 614-618.
L. Duca et al.; "The Elastin Receptor Complex Transduces Signals through the Catalytic Activity of Its Neu-1 Subunit"; The Journal of biological chemistry; Apr. 27, 2007; vol. 282; pp. 12484-12491.
C. Ntayi et al.; "Elastin-Derived Peptides Upregulate Matrix Metalloproteinase-2-ediated Melanoma Cell Invasion Through Elastin-Binding Protein"; The Journal of Investigative Dermatology; Feb. 2, 2004; vol. 122, pp. 256-265.
China National International Property Administration; International Search Report dated Aug. 20, 2021 issued in International Application No. PCT/CN2021/094680.

(Continued)

*Primary Examiner* — Sergio Coffa

(74) *Attorney, Agent, or Firm* — MASCHOFF BRENNAN

(57) ABSTRACT

The present invention relates to peptide compound targeting elastin-derived peptides and use thereof. The peptide comprises a parent peptide represented by the following amino acid sequence: $R_1$-Val-Xa2-Gly-Ser-Pro-Ser-Ala-Gln-Xa9-Xa10-Ala-Ser-Pro-Xa14, and is characterized by better biological activity, higher safety and stability, high synthesis yield, low cost, etc. The peptide compound may be used for treating hepatic fibrosis and fibrotic conditions accompanying hepatic disease as well as idiopathic pulmonary fibrosis and fibrotic conditions accompanying pulmonary disease.

9 Claims, 5 Drawing Sheets

Specification includes a Sequence Listing.

(56) References Cited

OTHER PUBLICATIONS

Arnaud Robinet et al., "Binding of elastin peptides to S-Gal protects the heart against is chemia/reperfusion injury by triggering the RISK pathway", The FASEB Journal • Research Communication, vol. 21, No. 9, pp. 1968-1978.
G. Moroy et al.,"A proposed interaction mechanism between elastin-derived peptides and the elastin/laminin receptor-binding domain", Proteins, vol. 76, No. 2, pp. 461-476.
Japan Patent Office; Office Action issued in JP App. No. 2023-516640 dated Nov. 2, 2023; 3 pages.

* cited by examiner

SEQUENCE LISTING

```
<160> NUMBER OF SEQ ID NOS: 26

<210> SEQ ID NO 1
<211> LENGTH: 14
<212> TYPE: PRT
<213> ORGANISM: Artificial Sequence
<220> FEATURE:
<223> OTHER INFORMATION: Compound 1

<400> SEQUENCE: 1

Val Val Gly Ser Pro Ser Ala Gln Asp Glu Ala Ser Pro Leu
1               5                   10


<210> SEQ ID NO 2
<211> LENGTH: 14
<212> TYPE: PRT
<213> ORGANISM: Artificial Sequence
<220> FEATURE:
<223> OTHER INFORMATION: Compound 2
```

-continued

<400> SEQUENCE: 2

Val Val Gly Ser Pro Ser Ala Gln Asp Glu Ala Ser Pro Ala
1 5 10

<210> SEQ ID NO 3
<211> LENGTH: 14
<212> TYPE: PRT
<213> ORGANISM: Artificial Sequence
<220> FEATURE:
<223> OTHER INFORMATION: Compound 3
<220> FEATURE:
<221> NAME/KEY: MISC_FEATURE
<222> LOCATION: (2)..(2)
<223> OTHER INFORMATION: Xaa=Isovaline

<400> SEQUENCE: 3

Val Xaa Gly Ser Pro Ser Ala Gln Asp Glu Ala Ser Pro Leu
1 5 10

<210> SEQ ID NO 4
<211> LENGTH: 14
<212> TYPE: PRT
<213> ORGANISM: Artificial Sequence
<220> FEATURE:
<223> OTHER INFORMATION: Compound 4

<400> SEQUENCE: 4

Val Val Gly Ser Pro Ser Ala Gln Glu Glu Ala Ser Pro Leu
1 5 10

<210> SEQ ID NO 5
<211> LENGTH: 14
<212> TYPE: PRT
<213> ORGANISM: Artificial Sequence
<220> FEATURE:
<223> OTHER INFORMATION: Compound 5
<220> FEATURE:
<221> NAME/KEY: MISC_FEATURE
<222> LOCATION: (2)..(2)
<223> OTHER INFORMATION: Xaa=Isovaline

<400> SEQUENCE: 5

Val Xaa Gly Ser Pro Ser Ala Gln Asp Glu Ala Ser Pro Ala
1 5 10

<210> SEQ ID NO 6
<211> LENGTH: 14
<212> TYPE: PRT
<213> ORGANISM: Artificial Sequence
<220> FEATURE:
<223> OTHER INFORMATION: Compound 6
<220> FEATURE:
<221> NAME/KEY: MISC_FEATURE
<222> LOCATION: (2)..(2)
<223> OTHER INFORMATION: Xaa=Isovaline

<400> SEQUENCE: 6

Val Xaa Gly Ser Pro Ser Ala Gln Asp Glu Ala Ser Pro Ala
1 5 10

<210> SEQ ID NO 7
<211> LENGTH: 14
<212> TYPE: PRT
<213> ORGANISM: Artificial Sequence
<220> FEATURE:
<223> OTHER INFORMATION: Compound 7
<220> FEATURE:
<221> NAME/KEY: MISC_FEATURE -continued
<222> LOCATION: (2)..(2)
<223> OTHER INFORMATION: Xaa=Isovaline

<400> SEQUENCE: 7

Val Xaa Gly Ser Pro Ser Ala Gln Glu Glu Ala Ser Pro Ala
1 5 10

<210> SEQ ID NO 8
<211> LENGTH: 14
<212> TYPE: PRT
<213> ORGANISM: Artificial Sequence
<220> FEATURE:
<223> OTHER INFORMATION: Compound 8
<220> FEATURE:
<221> NAME/KEY: MISC_FEATURE
<222> LOCATION: (2)..(2)
<223> OTHER INFORMATION: Xaa=Isovaline

<400> SEQUENCE: 8

Val Xaa Gly Ser Pro Ser Ala Gln Glu Glu Ala Ser Pro Ala
1 5 10

<210> SEQ ID NO 9
<211> LENGTH: 14
<212> TYPE: PRT
<213> ORGANISM: Artificial Sequence
<220> FEATURE:
<223> OTHER INFORMATION: Compound 9
<220> FEATURE:
<221> NAME/KEY: MISC_FEATURE
<222> LOCATION: (2)..(2)
<223> OTHER INFORMATION: Xaa=Isovaline

<400> SEQUENCE: 9

Val Xaa Gly Ser Pro Ser Ala Gln Glu Asp Ala Ser Pro Ala
1 5 10

<210> SEQ ID NO 10
<211> LENGTH: 15
<212> TYPE: PRT
<213> ORGANISM: Artificial Sequence
<220> FEATURE:
<223> OTHER INFORMATION: Compound 10

<400> SEQUENCE: 10

Glu Val Val Gly Ser Pro Ser Ala Gln Glu Asp Ala Ser Pro Ala
1 5 10 15

<210> SEQ ID NO 11
<211> LENGTH: 14
<212> TYPE: PRT
<213> ORGANISM: Artificial Sequence
<220> FEATURE:
<223> OTHER INFORMATION: Compound 11
<220> FEATURE:
<221> NAME/KEY: MISC_FEATURE
<222> LOCATION: (2)..(2)
<223> OTHER INFORMATION: Xaa=Isovaline

<400> SEQUENCE: 11

Val Xaa Gly Ser Pro Ser Ala Gln Glu Glu Ala Ser Pro Leu
1 5 10

<210> SEQ ID NO 12
<211> LENGTH: 14
<212> TYPE: PRT
<213> ORGANISM: Artificial Sequence
<220> FEATURE:
<223> OTHER INFORMATION: Compound 12

-continued

<400> SEQUENCE: 12

Val Val Gly Ser Pro Ser Ala Gln Glu Asp Ala Ser Pro Leu
1 5 10

<210> SEQ ID NO 13
<211> LENGTH: 14
<212> TYPE: PRT
<213> ORGANISM: Artificial Sequence
<220> FEATURE:
<223> OTHER INFORMATION: Compound 13
<220> FEATURE:
<221> NAME/KEY: MISC_FEATURE
<222> LOCATION: (2)..(2)
<223> OTHER INFORMATION: Xaa=Isovaline

<400> SEQUENCE: 13

Val Xaa Gly Ser Pro Ser Ala Gln Glu Glu Ala Ser Pro Ala
1 5 10

<210> SEQ ID NO 14
<211> LENGTH: 14
<212> TYPE: PRT
<213> ORGANISM: Artificial Sequence
<220> FEATURE:
<223> OTHER INFORMATION: Compound 14
<220> FEATURE:
<221> NAME/KEY: MISC_FEATURE
<222> LOCATION: (2)..(2)
<223> OTHER INFORMATION: Xaa=Isovaline

<400> SEQUENCE: 14

Val Xaa Gly Ser Pro Ser Ala Gln Glu Glu Ala Ser Pro Ala
1 5 10

<210> SEQ ID NO 15
<211> LENGTH: 14
<212> TYPE: PRT
<213> ORGANISM: Artificial Sequence
<220> FEATURE:
<223> OTHER INFORMATION: Compound 15
<220> FEATURE:
<221> NAME/KEY: MISC_FEATURE
<222> LOCATION: (2)..(2)
<223> OTHER INFORMATION: Xaa=Isovaline

<400> SEQUENCE: 15

Val Xaa Gly Ser Pro Ser Ala Gln Glu Glu Ala Ser Pro Ala
1 5 10

<210> SEQ ID NO 16
<211> LENGTH: 14
<212> TYPE: PRT
<213> ORGANISM: Artificial Sequence
<220> FEATURE:
<223> OTHER INFORMATION: Compound 16
<220> FEATURE:
<221> NAME/KEY: MISC_FEATURE
<222> LOCATION: (2)..(2)
<223> OTHER INFORMATION: Xaa=Isovaline

<400> SEQUENCE: 16

Val Xaa Gly Ser Pro Ser Ala Gln Asp Glu Ala Ser Pro Ala
1 5 10

<210> SEQ ID NO 17
<211> LENGTH: 14
<212> TYPE: PRT
<213> ORGANISM: Artificial Sequence

```
<220> FEATURE:
<223> OTHER INFORMATION: Compound 17

<400> SEQUENCE: 17

Val Val Gly Ser Pro Ser Ala Gln Asp Glu Ala Ser Pro Leu
1               5                   10


<210> SEQ ID NO 18
<211> LENGTH: 14
<212> TYPE: PRT
<213> ORGANISM: Artificial Sequence
<220> FEATURE:
<223> OTHER INFORMATION: Compound 18

<400> SEQUENCE: 18

Val Val Gly Ser Pro Ser Ala Gln Asp Glu Ala Ser Pro Ala
1               5                   10


<210> SEQ ID NO 19
<211> LENGTH: 14
<212> TYPE: PRT
<213> ORGANISM: Artificial Sequence
<220> FEATURE:
<223> OTHER INFORMATION: Compound 19
<220> FEATURE:
<221> NAME/KEY: MISC_FEATURE
<222> LOCATION: (2)..(2)
<223> OTHER INFORMATION: Xaa=Isovaline

<400> SEQUENCE: 19

Val Xaa Gly Ser Pro Ser Ala Gln Asp Glu Ala Ser Pro Leu
1               5                   10


<210> SEQ ID NO 20
<211> LENGTH: 14
<212> TYPE: PRT
<213> ORGANISM: Artificial Sequence
<220> FEATURE:
<223> OTHER INFORMATION: Compound 20

<400> SEQUENCE: 20

Val Val Gly Ser Pro Ser Ala Gln Glu Glu Ala Ser Pro Leu
1               5                   10


<210> SEQ ID NO 21
<211> LENGTH: 14
<212> TYPE: PRT
<213> ORGANISM: Artificial Sequence
<220> FEATURE:
<223> OTHER INFORMATION: Compound 21
<220> FEATURE:
<221> NAME/KEY: MISC_FEATURE
<222> LOCATION: (2)..(2)
<223> OTHER INFORMATION: Xaa=Isovaline

<400> SEQUENCE: 21

Val Xaa Gly Ser Pro Ser Ala Gln Asp Glu Ala Ser Pro Ala
1               5                   10


<210> SEQ ID NO 22
<211> LENGTH: 14
<212> TYPE: PRT
<213> ORGANISM: Artificial Sequence
<220> FEATURE:
<223> OTHER INFORMATION: Compound 22
<220> FEATURE:
<221> NAME/KEY: MISC_FEATURE
<222> LOCATION: (2)..(2)
<223> OTHER INFORMATION: Xaa=Isovaline
```

-continued

```
<400> SEQUENCE: 22

Val Xaa Gly Ser Pro Ser Ala Gln Glu Glu Ala Ser Pro Ala
1               5                   10


<210> SEQ ID NO 23
<211> LENGTH: 14
<212> TYPE: PRT
<213> ORGANISM: Artificial Sequence
<220> FEATURE:
<223> OTHER INFORMATION: Compound 23
<220> FEATURE:
<221> NAME/KEY: MISC_FEATURE
<222> LOCATION: (2)..(2)
<223> OTHER INFORMATION: Xaa=Isovaline

<400> SEQUENCE: 23

Val Xaa Gly Ser Pro Ser Ala Gln Glu Asp Ala Ser Pro Leu
1               5                   10


<210> SEQ ID NO 24
<211> LENGTH: 14
<212> TYPE: PRT
<213> ORGANISM: Artificial Sequence
<220> FEATURE:
<223> OTHER INFORMATION: Compound 24

<400> SEQUENCE: 24

Val Val Gly Ser Pro Ser Ala Gln Glu Asp Ala Ser Pro Ala
1               5                   10


<210> SEQ ID NO 25
<211> LENGTH: 14
<212> TYPE: PRT
<213> ORGANISM: Artificial Sequence
<220> FEATURE:
<223> OTHER INFORMATION: Compound 25
<220> FEATURE:
<221> NAME/KEY: MISC_FEATURE
<222> LOCATION: (2)..(2)
<223> OTHER INFORMATION: Xaa=Isovaline

<400> SEQUENCE: 25

Val Xaa Gly Ser Pro Ser Ala Gln Glu Asp Ala Ser Pro Ala
1               5                   10


<210> SEQ ID NO 26
<211> LENGTH: 14
<212> TYPE: PRT
<213> ORGANISM: Artificial Sequence
<220> FEATURE:
<223> OTHER INFORMATION: The parent peptide of the peptide compound
      targeting elastin-derived peptides
<220> FEATURE:
<221> NAME/KEY: MISC_FEATURE
<222> LOCATION: (2)..(2)
<223> OTHER INFORMATION: Xaa=Val or Isovaline
<220> FEATURE:
<221> NAME/KEY: MISC_FEATURE
<222> LOCATION: (9)..(9)
<223> OTHER INFORMATION: Xaa=Asp or Glu
<220> FEATURE:
<221> NAME/KEY: MISC_FEATURE
<222> LOCATION: (10)..(10)
<223> OTHER INFORMATION: Xaa=Glu or Asp
<220> FEATURE:
<221> NAME/KEY: MISC_FEATURE
<222> LOCATION: (14)..(14)
<223> OTHER INFORMATION: Xaa=Leu or Isovaline
```

-continued

```
<400> SEQUENCE: 26

Val Xaa Gly Ser Pro Ser Ala Gln Xaa Xaa Ala Ser Pro Xaa
1               5                   10
```

PEPTIDE COMPOUND TARGETING ELASTIN-DERIVED PEPTIDES AND USE THEREOF

CROSS-REFERENCE

The present application is a nationalization of PCT Application No. PCT/CN2021/094680 filed May 19, 2021, which claims priority to Chinese Application No. 202010515052.8 filed on Jun. 8, 2020, which applications are incorporated herein by specific reference in their entirety.

SEQUENCE LISTING

This application contains a Sequence Listing which has been submitted in ASCII format and is hereby incorporated by reference in its entirety. The ASCII copy, is named L1211-10053US01_SequenceListing created on Apr. 27, 2023 and is 7666 bytes in size.

TECHNICAL FIELD OF THE INVENTION

The present invention belongs to the field of biochemical technology, and specifically, the present invention relates to the peptide compound targeting elastin-derived peptides (EDPs). The peptide compound may be used in the preparation of a drug for preventing or treating organ fibrosis and fibrotic conditions accompanying organ disease, especially hepatic fibrosis and fibrotic conditions accompanying hepatic disease as well as idiopathic pulmonary fibrosis and fibrotic conditions accompanying pulmonary disease.

BACKGROUND OF THE INVENTION

Organ fibrosis is a characteristic sign of end-stage organ failure in many chronic diseases, which is a serious danger to the physical health of the general public and a major cause of death in patients. At present, it is believed that the main mechanism of fibrosis is the initiation of the protective repair process by the body to cope with injurious irritation, but the repeated aberrant healing and repair lead to a disorder of the environment inside the tissue, the excessive accumulation of the extracellular matrix (ECM) and the damage of tissue structure, thus causing fibrosis (D. C. Rockey, P. D. Bell, J. A. Hill, *The New England journal of medicine* 2015, 372, 1138-1149.).

Feature of organ fibrosis occurs at the terminal stage of many chronic diseases, for instance, hepatic fibrosis is a pathological process caused by the unbalanced deposition of the matrix due to the continual synthesis and degradation of the ECM when the tissue makes repair responses to the continual liver injury and is also a dynamic process involving complex cellular and molecular mechanisms. Hepatic fibrosis is a major pathological feature of chronic liver diseases and also the main intermediate link before the further development into hepatic cirrhosis. The repair response to injury causes many changes to the ECM microenvironment, during which the quiescent hepatic stellate cells are activated, leading to changes in the forms and functions of hepatic stellate cells, specifically, the abnormal synthesis and degradation of the ECM (L. Petitclerc, G. Sebastiani, G. Gilbert, G. Cloutier, A. Tang, Journal of magnetic resonance imaging: JMR/2017, 45, 1276-1295.). An imbalance in ECM synthesis and degradation leads to the massive accumulation of the ECM and thus the formation of fibrosis. The occurrence of fibrosis further increases the activation of hepatic stellate cells, which aggravates fibrosis continually. There are many causes of hepatic fibrosis and cirrhosis, for example, in western countries, the most common inducing factors are overdrinking, hepatitis virus infection and fatty liver disease. In addition, chronic immune-mediated injury can also lead to hepatic fibrosis and cirrhosis, such as primary sclerosing cholangitis (PSC), primary biliary cholangitis (PBC) and autoimmune hepatitis (AIH) (K. Bottcher, M. Pinzani, *Advanced drug delivery reviews* 2017, 121, 3-8.).

Hepatic fibrosis, if not controlled and treated, will develop into hepatic cirrhosis and finally result in impaired liver function and hepatonecrosis. Once hepatic cirrhosis develops in patients, they will be at a very high risk of hepatocellular carcinoma (A. H. Ali, K. D. Lindor, *Expert opinion on pharmacotherapy* 2016, 17, 1809-1815.), suffer great pain and even have their lives threatened; consequently, they must be treated by liver transplantation. It is thus clear that hepatic fibrosis poses a serious threat to the health of the people of China and the world and needs to be treated with an effective drug!

However, up to now, the only drug approved by the Food and drug Administration (FDA) for the treatment of fibrosis has been obeticholic acid (OCA). Nevertheless, there are prominent adverse reactions including itching and a decrease in high density lipoprotein cholesterol during the treatment with OCA. Some patients are even forced to discontinue medication due to pruritus, and others may have severe cardiovascular events. At present, OCA is expensive, and pharmacoeconomic analysis suggests that OCA is not optimistic in terms of the cost-effectiveness ratio and still needs to be further optimized and improved. Based on the above reasons, it appears to be particularly important to research and develop a fibrosis treatment drug that has fewer side effects and is more targeted and economical.

Another common concern is the occurrence of pulmonary fibrosis. Idiopathic pulmonary fibrosis (IPF) is a chronic, progressive and fibrotic interstitial pneumonia, the cause and pathogenesis of which are unknown and which are characterized by pulmonary remodeling caused by the aberrant deposition of ECM (L. Richeldi, H. R. Collard, M. G. Jones, *The Lancet* 2017, 389, 1941-1952.). This disease is common in the elderly, with a median survival rate of 2-3 years. The pathogenesis and risk factors include genetic factors, environmental exposure, smoking, chronic viral infection and some complications. The histopathological examination often reveals the extensive formation of alveolar scars, namely normal alveoli are replaced by fibrous scars containing myofibroblasts. IPF cannot be cured and the purpose of treatment is to slow disease progression, improve the quality of life and prolong life, including treatment of pulmonary fibrosis with anti-fibrosis drug such as nintedanib and pirfenidone, and non-drug treatment (D. J. Lederer, F. J. Martinez, *The New England journal of medicine* 2018, 378, 1811-1823.). Although new progress has been made in our understanding of IPF pathology, there is still no method to treat IPF, and the currently available anti-fibrosis treatment methods only slow, but cannot completely stop, the disease progression.

In addition, in terms of the cause of pulmonary fibrosis, chronic obstructive pulmonary disease (COPD) is a common disease with high global morbidity and mortality, which has such characteristics as small airway obstruction (chronic obstructive bronchiolitis) and emphysema. It is confirmed by airway examination that the reversibility of airway obstruction is poor, which leads to air trapping in the lungs and shortness of breath in response to physical activities. The most common risk factor for COPD is smoking. Despite the fact that the mechanism of COPD is still poorly understood, the disease is related to chronic inflammation that is usually resistant to corticosteroids. Besides, COPD involves accelerated ageing of the lungs and an abnormal repair mechanism that might be driven by oxidative stress (K. F. Rabe, H. Watz, *The Lancet* 2017, 389, 1931-1940.). In addition to encouraging smoking cessation, effective long-acting bronchodilator agents and home oxygen therapy can control and keep the disease inactive, but these drugs cannot slow down the potential disease process and thus will not reduce the disease progression or mortality. More research is needed to better understand the mechanism of the disease and develop new therapy to reduce the disease activity and progression.

Elastin is the most stable protein in ECM and a major component of elastic fiber. It is present in various elastic soft tissues such as artery walls, ligaments, lungs, bladders and skin (ROBERT M. SENIOR, *J. Clin. Invest.* 1982, 70, 614-618.). Elastin synthesis is initiated during the fetal period, reaches its peak at the time of birth, and gradually decreases and even disappears after puberty. The half-life of elastic fiber is as long as 70 years, and the rate of synthesis is low. In a normal pathological state, elastic fibers are the main components for tissue connection, which are used to maintain the elasticity of tissue. However, in the pathological state of a disease, elastic fibers will be abnormally synthesized and degraded. The degradation of elastic fibers produces a series of derived peptides (EDPs) that have different amino acid sequences and activate downstream receptors to regulate a range of cell signals, such as Ras-Raf-1-MEK1/2-ERK1/2; Gi-p110γ-Raf-1-MEK1/2-ERK1/2; CAMP-PKA-B-Raf-MEK1/2-ERK1/2; NO-CGMP-PKG-Raf-1-MEK1/2-ERK1/2 or Gi-p110γ-Akt-caspase9-Bad-Foxo3A (L. Duca, C. Blanchevoye, B. Cantarelli, C. Ghoneim, S. Dedieu, F. Delacoux, W. Hornebeck, A. Hinek, L. Martiny, L. Debelle, *The Journal of biological chemistry* 2007, 282, 12484-12491.). EDPs are closely related to the development of many diseases. Research has found that the excessive production of EDPs can lead to metabolic disorders of the liver and the accumulation of inflammation, thus promoting the development of hepatic diseases. Therefore, inhibiting the activity of EDPs will certainly relieve hepatic fibrosis to some extent (C. Ntayi, A. L. Labrousse, R. Debret, P. Birembaut, G. Bellon, F. Antonicelli, W. Hornebeck, P. Bernard, *The Journal of investigative dermatology* 2004, 122, 256-265.). Although the pathogenesis of IPF is still unclear, abnormal ECM remodeling is considered conducive to the continuous deposition of collagenous pulmonary scar tissues. It is speculated in research that the abnormal remodeling of ECM plays an important role in the development and (or) progression of diseases.

In conclusion, the current drugs under clinical research are still deficient and of safety risks to treat fibrotic diseases. It is still an arduous scientific task to research and develop safer and more effective new targeted drugs in the anti-fibrosis field, and the design and synthesis of corresponding pharmaceutical molecules are imminent!

The present invention relates to a novel peptide compound targeting elastin-derived peptides (EDPs), which may be combined with the EDPs circulating in the body to block their biological effects. A series of active peptides is pharmacodynamically evaluated by screening the activities of cell models in vitro and animal models in vivo. At present, there is no similar research report on the correlation between compounds and fibrosis in the art. Therefore, on the basis of the conformation and binding site of EDPs, the present invention designs a bioactive peptide compound binding EDPs, which is bound to provide a new idea and scientific research direction in the research and development of drugs for treating organ fibrosis.

SUMMARY OF THE INVENTION

The purpose of the present invention is to provide a novel peptide compound targeting elastin-derived peptides. The present invention has been proved by a large number of experimental studies that the peptide compound has no adverse reactions and can be used for treating organ fibrosis and fibrotic conditions accompanying organ diseases; preferably, the organ fibrosis and fibrotic conditions accompanying organ diseases are: hepatic fibrosis, fibrotic conditions accompanying hepatic diseases, idiopathic pulmonary fibrosis and fibrotic conditions accompanying pulmonary diseases.

Another purpose of the present invention is to provide an application of the novel peptide compound for preventing or treating the organ fibrosis and fibrotic conditions accompanying organ diseases, and particularly the novel peptide compound can be used as a new generation drug to treat hepatic fibrosis, fibrotic conditions accompanying hepatic diseases, idiopathic pulmonary fibrosis and fibrotic conditions accompanying pulmonary diseases.

The technical solution of the present invention is as follows:

The present invention provides peptide compound targeting elastin-derived peptides comprising a parent peptide represented by the following amino acid sequence:

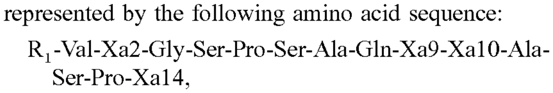

$R_1$-Val-Xa2-Gly-Ser-Pro-Ser-Ala-Gln-Xa9-Xa10-Ala-Ser-Pro-Xa14, wherein, $R_1$ is a lipophilic substituent or is absent;

Xa2=Val or Iva;

Xa9=Asp or Glu;

Xa10=Glu or Asp;

Xa14=Leu or Ala;

when $R_1$ is absent, Xa2=Val and Xa14=Leu, the parent peptide is a non-linear peptide.

Wherein the amino group of Val at position 1 in the amino acid sequence of the parent peptide is attached to the lipophilic substituent via a bridging group when $R_1$ is a lipophilic substituent, the bridging group comprises $(PEG)_m$, or $(PEG)_m$ and γGlu or $(PEG)_m$ and Asp, and the linkage is that the amino group of Val at position 1 is attached to the lipophilic substituent via the PEGylation of $(PEG)_m$ in the bridging group; moreover, the lipophilic substituent is $CH_3(CH_2)_nC(O)$— or $HOOC(CH_2)_nC(O)$—, and the acyl thereof and the amino contained in the bridging group form an amido bond; wherein m is an integer of 2 to 10, and n is an integer of 14-20; the carboxyl terminal of the amino acid sequence is a bare carboxyl group or is attached to an amino group to form a —$CONH_2$ group. The linkage is as shown on FIG. 7.

Wherein the amino group of Val at position 1 and the carboxyl group of the amino acid at position 14 in the amino acid sequence of the parent peptide form an amido bond to make up a cyclic peptide compound when $R_1$ is absent; the cyclic peptide compound is shown as follows:

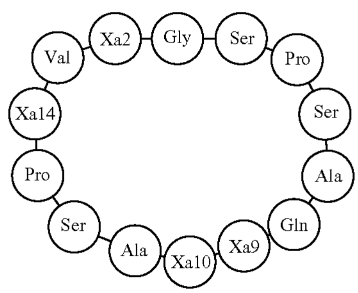 [SMILES: C1CCCCCCCCCCCCC1]

Xa2=Val or Iva;
Xa9=Asp or Glu;
Xa10=Glu or Asp;
Xa14=Leu or Ala.

According to the specific embodiment of the present invention, the amino acid sequence of the parent peptide is selected from SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24 and SEQ ID NO. 25.

According to the specific embodiment of the present invention, the structure linked to the amino group of Val at position 1 in the amino acid sequence of the parent peptide is:

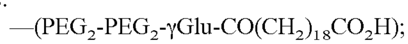
—($PEG_2$-$PEG_2$-γGlu-$CO(CH_2)_{18}CO_2H$);

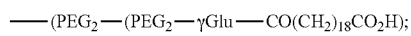
—($PEG_2$—($PEG_2$—γGlu—$CO(CH_2)_{18}CO_2H$);

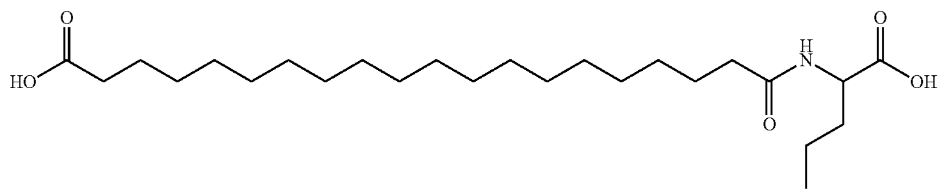

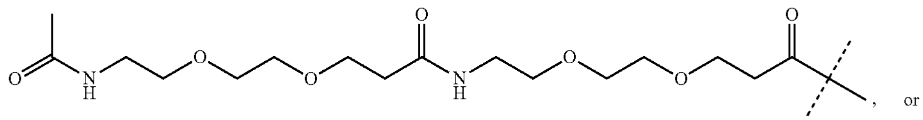
, or

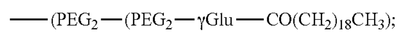
—($PEG_2$—($PEG_2$—γGlu—$CO(CH_2)_{18}CH_3$);

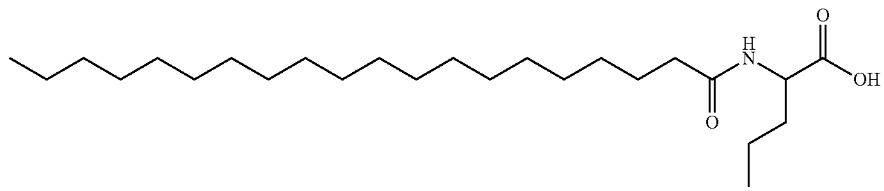

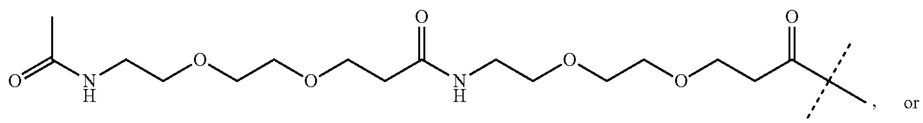
, or

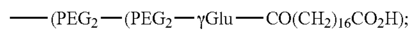
—($PEG_2$—($PEG_2$—γGlu—$CO(CH_2)_{16}CO_2H$);

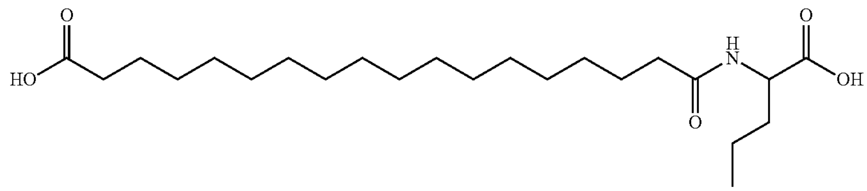

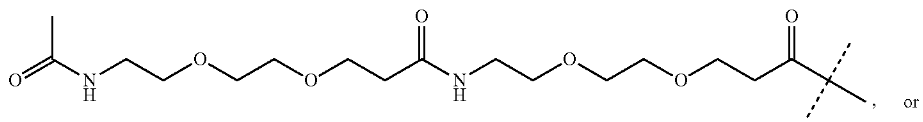
, or

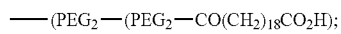
—($PEG_2$—($PEG_2$—$CO(CH_2)_{18}CO_2H$);

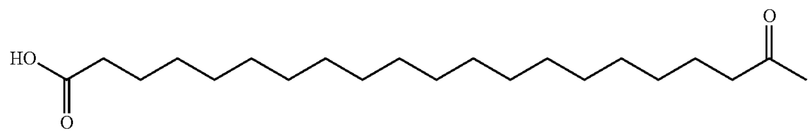

-continued

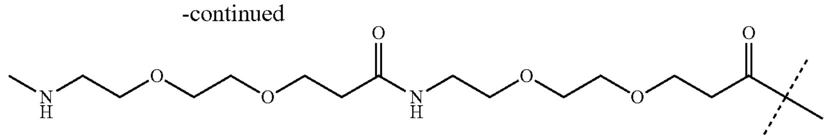

According to the specific embodiment of the present invention, the present invention provides any of the following peptide compounds:

Compound 1 (SEQ ID NO. 1): ($PEG_2$-$PEG_2$-γGlu-CO($CH_2$)$_{18}$$CO_2$H)-Val-Val-Gly-Ser-Pro-Ser-Ala-Gln-Asp-Glu-Ala-Ser-Pro-Leu-$NH_2$ Compound 2 (SEQ ID NO. 2): ($PEG_2$-$PEG_2$-γGlu-CO($CH_2$)$_{18}$$CO_2$H)-Val-Val-Gly-Ser-Pro-Ser-Ala-Gln-Asp-Glu-Ala-Ser-Pro-Ala-$NH_2$ Compound 3 (SEQ ID NO. 3): ($PEG_2$-$PEG_2$-γGlu-CO($CH_2$)$_{18}$$CO_2$H)-Val-Iva-Gly-Ser-Pro-Ser-Ala-Gln-Asp-Glu-Ala-Ser-Pro-Leu-$NH_2$ Compound 4 (SEQ ID NO. 4): ($PEG_2$-$PEG_2$-γGlu-CO($CH_2$)$_{18}$$CO_2$H)-Val-Val-Gly-Ser-Pro-Ser-Ala-Gln-Glu-Glu-Ala-Ser-Pro-Leu-$NH_2$ Compound 5 (SEQ ID NO. 5): ($PEG_2$-$PEG_2$-γGlu-CO($CH_2$)$_{18}$$CO_2$H)-Val-Iva-Gly-Ser-Pro-Ser-Ala-Gln-Asp-Glu-Ala-Ser-Pro-Ala-$NH_2$ Compound 6 (SEQ ID NO. 6): ($PEG_2$-$PEG_2$-γGlu-CO($CH_2$)$_{18}$$CO_2$H)-Val-Iva-Gly-Ser-Pro-Ser-Ala-Gln-Asp-Glu-Ala-Ser-Pro-Ala Compound 7 (SEQ ID NO. 7): ($PEG_2$-$PEG_2$-γGlu-CO($CH_2$)$_{18}$$CO_2$H)-Val-Iva-Gly-Ser-Pro-Ser-Ala-Gln-Glu-Glu-Ala-Ser-Pro-Ala-$NH_2$ Compound 8 (SEQ ID NO. 8): ($PEG_2$-$PEG_2$-γGlu-CO($CH_2$)$_{18}$$CO_2$H)-Val-Iva-Gly-Ser-Pro-Ser-Ala-Gln-Glu-Glu-Ala-Ser-Pro-Ala Compound 9 (SEQ ID NO. 9): ($PEG_2$-$PEG_2$-γGlu-CO($CH_2$)$_{18}$$CO_2$H)-Val-Iva-Gly-Ser-Pro-Ser-Ala-Gln-Glu-Asp-Ala-Ser-Pro-Ala-$NH_2$ Compound 10 (SEQ ID NO. 10): ($PEG_2$-$PEG_2$-γGlu-CO($CH_2$)$_{18}$$CO_2$H)-Val-Val-Gly-Ser-Pro-Ser-Ala-Gln-Glu-Asp-Ala-Ser-Pro-Ala-$NH_2$ Compound 11 (SEQ ID NO. 11): ($PEG_2$-$PEG_2$-γGlu-CO($CH_2$)$_{18}$$CO_2$H)-Val-Iva-Gly-Ser-Pro-Ser-Ala-Gln-Glu-Glu-Ala-Ser-Pro-Leu-$NH_2$ Compound 12 (SEQ ID NO. 12): ($PEG_2$-$PEG_2$-γGlu-CO($CH_2$)$_{18}$$CO_2$H)-Val-Val-Gly-Ser-Pro-Ser-Ala-Gln-Glu-Asp-Ala-Ser-Pro-Leu-$NH_2$ Compound 13 (SEQ ID NO. 13): ($PEG_2$-$PEG_2$-γGlu-CO($CH_2$)$_{18}$$CH_3$)-Val-Iva-Gly-Ser-Pro-Ser-Ala-Gln-Glu-Glu-Ala-Ser-Pro-Ala-$NH_2$ Compound 14 (SEQ ID NO. 14): ($PEG_2$-$PEG_2$-γGlu-CO($CH_2$)$_{16}$$CO_2$H)-Val-Iva-Gly-Ser-Pro-Ser-Ala-Gln-Glu-Glu-Ala-Ser-Pro-Ala-$NH_2$ Compound 15 (SEQ ID NO. 15): ($PEG_2$-$PEG_2$-CO($CH_2$)$_{18}$$CO_2$H)-Val-Iva-Gly-Ser-Pro-Ser-Ala-Gln-Glu-Glu-Ala-Ser-Pro-Ala-$NH_2$ Compound 16 (SEQ ID NO. 16): ($PEG_2$-$PEG_2$-CO($CH_2$)$_{18}$$CO_2$H)-Val-Iva-Gly-Ser-Pro-Ser-Ala-Gln-Asp-Glu-Ala-Ser-Pro-Ala-$NH_2$ Compound 17 (SEQ ID NO. 17):

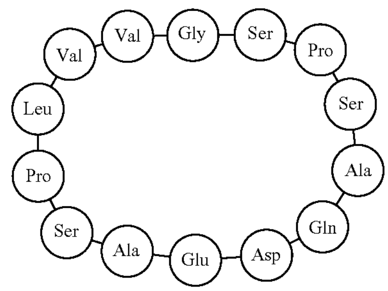 [SMILES: C1CCCCCCCCCCCCC1]

Compound 18 (SEQ ID NO. 18):

-continued

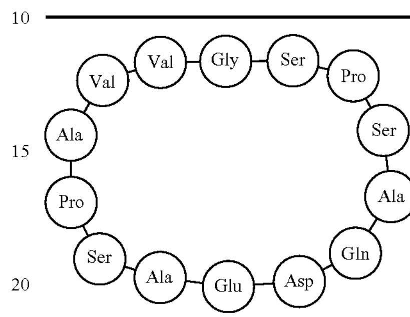

Compound 19 (SEQ ID NO. 19):

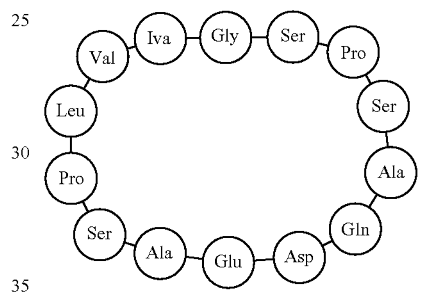

Compound 20 (SEQ ID NO. 20):

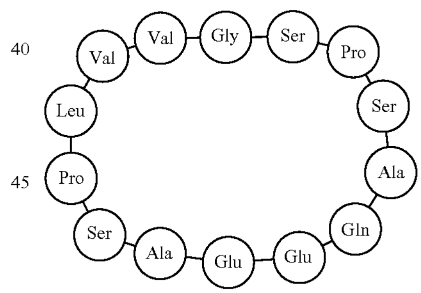

Compound 21 (SEQ ID NO. 21):

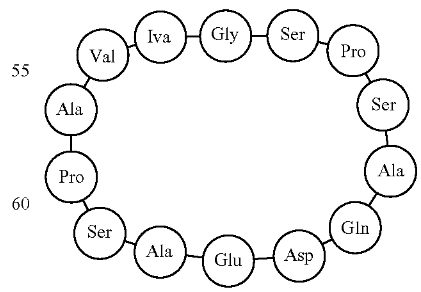

Compound 22 (SEQ ID NO. 22):

-continued

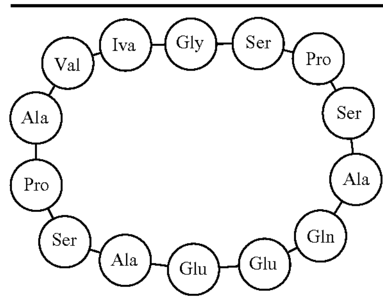

Compound 23 (SEQ ID NO. 23):

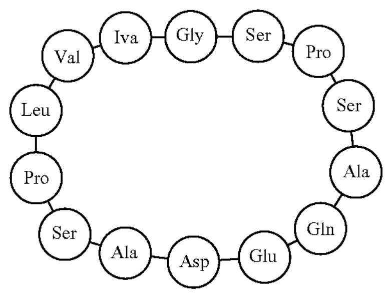 [SMILES: C1CCCCCCCCCCCCC1]

Compound 24 (SEQ ID NO. 24):

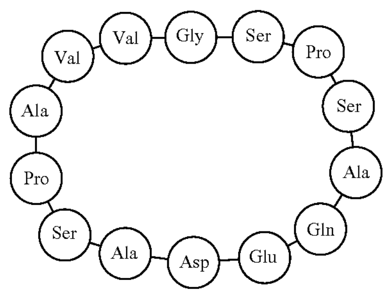 [SMILES: C1CCCCCCCCCCCCC1]

Compound 25 (SEQ ID NO. 25):

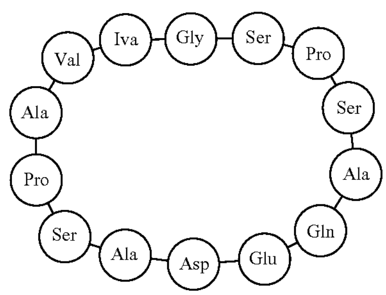 [SMILES: C1CCCCCCCCCCCCC1]

Another aspect of the present invention is to provide a pharmaceutical composition containing the novel peptide compound of the present invention, and the pharmaceutical composition is made by adding pharmaceutically acceptable carriers and/or excipients with the novel peptide compound as the active ingredient.

Yet another aspect of the present invention is to provide a use of the novel peptide compound. Cell and animal experiments show that, the novel peptide compound of the present invention has no adverse reactions and can be used for treating organ fibrosis and fibrotic conditions accompanying organ diseases; preferably, the organ fibrosis and fibrotic conditions accompanying organ diseases are: hepatic fibrosis, fibrotic conditions accompanying hepatic diseases, idiopathic pulmonary fibrosis and fibrotic conditions accompanying pulmonary diseases.

The parent peptide in the novel peptide compound mentioned in the present invention is a homologous polypeptide. The homologous polypeptide in the present invention refers to that the polypeptide originally has the amino acid sequence of the natural parent peptide, but one or more amino acid residues have been substituted by different amino acid residues, and these amino acid residues are conservative with each other. The obtained polypeptide can be used to implement the present invention. In addition, the cell and animal experiments show that the parent peptide in the peptide compound of the present invention has better biological and pharmaceutical activities than the natural parent peptide in the same mass number, and its therapeutic effect is better than the natural parent peptide.

It will be understood by those of skill in the art that the pharmaceutical compositions of the present invention are suitable for various modes of administration, such as oral administration, transdermal administration, intravenous administration, intramuscular administration, topical administration, transnasal administration, etc. Depending on the mode of administration used, the pharmaceutical compositions of the peptide of the present invention can be made in various suitable dosage forms comprising at least an effective dose of the peptide of the present invention and at least a pharmaceutically acceptable pharmaceutical carrier. Examples of suitable dosage forms are tablets, capsules, sugar-coated tablets, granules, oral solutions and syrups, ointments and patches for skin surfaces, aerosols, nasal sprays, and sterile solutions that can be used for injection . . .

The pharmaceutical composition comprising the peptide of the present invention can be made into solutions or lyophilized powders for parenteral administration, and the powders can be reconfigured by adding appropriate solvents or other pharmaceutical carriers prior to use, and the liquid formulations are generally buffers, isotonic solutions, and aqueous solutions.

The dosage of the pharmaceutical composition of the present invention may vary within a wide range and can be easily determined by those skilled in the art according to certain factors such as the type of the disease, the severity of the disease, patient's body weight, the dosage form, the administration route.

The present invention has the following advantages:

1) Better bioactivities than the natural parent peptide in the same mass number;
2) Better therapeutic effects of treating hepatic fibrosis and fibrotic conditions accompanying hepatic disease as well as idiopathic pulmonary fibrosis and fibrotic conditions accompanying pulmonary disease than the natural parent peptide in the same mass number;
3) More prominent pharmaceutical activity in pharmacokinetic experiments of drugs than the natural parent peptide in the same mass number;
4) Better safety and stability in pharmacokinetic experiments of drugs than the natural parent peptide in the same mass number;
5) High synthesis yield, good stability, easy to scale-up and low cost.

The abbreviations used in the present invention are defined as follows:

Boc is tert-butyloxycarboryl, Fmoc is fluorenylmethoxycarbonyl, t-Bu is tert-butyl, resin is colophony, TFA is trifluoroacetic acid, EDT is 1,2-ethanedithiol, FBS is fetal bovine serum, BSA is bovine serum albumin, HPLC is high performance liquid chromatograph, mPEG is mono-methoxy-polyethylene diol, Ser is serine, D-Ser is D-serine, Gln is glutamine, Gly is glycine, Glu is Glutamic acid, Ala is Alanine, Asp is Aspartic acid, Leu is Leucine, Pro is Proline, Val is Valine, and Iva is isovaline.

DETAILED DESCRIPTION OF THE PREFERRED EMBODIMENTS

Figure 1:
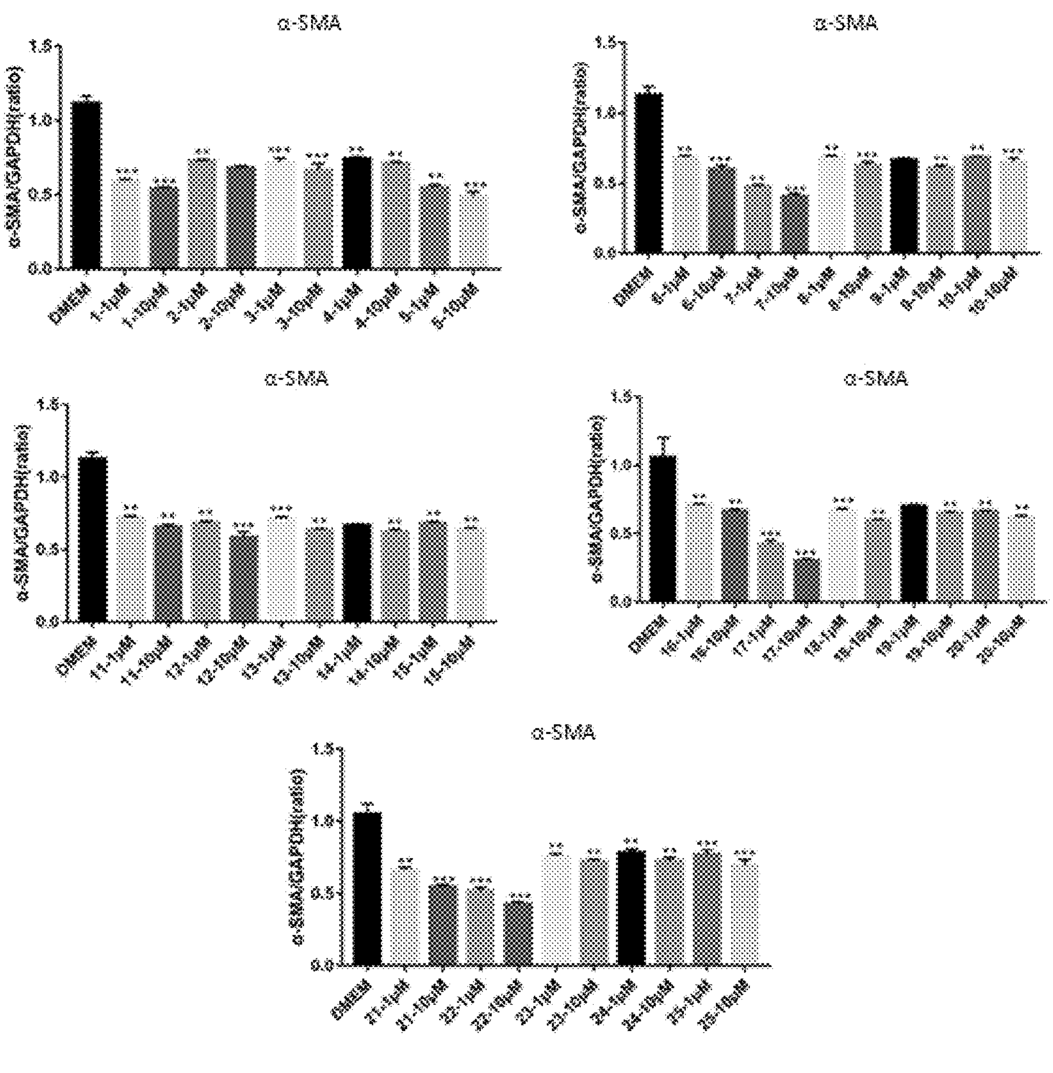
FIG. 1 is a statistical histogram for activity evaluation of compounds 1-25 in the LX2 cell model in Embodiment 2 ( indicates that the confidence level is >99%, and the difference between the two is very significant (P<0.01); * indicates that the confidence level is >99.9%, and the difference between the two is extremely significant (P<0.001).

The embodiments of the present invention will be described in detail hereafter in conjunction with the examples, it will be understood by those skilled in the art will appreciate that the following embodiments are only intended to illustrate the invention and should not be considered as limiting the scope of the invention. Where specific conditions are not indicated in the embodiments, they are carried out according to conventional conditions or those recommended by the manufacturer. Where the manufacturer is not specified for the reagents or apparatus used, they are conventional products available commercially.

Embodiment 1 Synthesis of a Peptide

Take the synthesis of peptide compounds 7 and 22 as an example.

Materials:

All amino acids are purchased from GL Biochem (Shanghai) Ltd., and the resin is Rink Amide MBHA (loading-0.36 mmol/g) from Sunresin New Materials Co. Ltd., Xi'an. Unless otherwise specified, other reagents are all analytically pure and purchased from Shanghai Titan Scientific Co., Ltd. Phenomenex Luna C18 preparative column (20 mm×250 mm) is used to purify the peptides. HPLC is from Thermofisher, and the model is Ultimate 3000. The mass spectrum is determined by using Agilent mass spectrometer with the model of 1260-6120.

Methods:

1. Synthesis of a Peptide Compound 7:

Structure Sequence:

($PEG_2$-$PEG_2$-γGlu-$CO(CH_2)_{18}CO_2H$)-Val-Iva-Gly-Ser-Pro-Ser-Ala-Gln-Glu-Glu-Ala-Ser-Pro-Ala-$NH_2$

1) Coupling of Peptide Resin:

The following peptides with the scale of 0.72 mmol are synthesized on a peptide synthesizer according to Fmoc protection strategy:

($PEG_2$-$PEG_2$-γGlu(OtBu)—$CO(CH_2)_{18}CO$(OtBu))-Val-Iva-Gly-Ser(tBu)-Pro-Ser(tBu)-Ala-Gln (Trt)-Glu (OtBu)-Glu(OtBu)-Ala-Ser(tBu)-Pro-Ala-Rink Amide MBHA peptide resin (1) Step 1: Resin Swelling 2 g Rink amide MBHA resin is swelled in N,N-dimethyl formamide (DMF), and the resin is swelled with N,N-dimethyl formamide for twice, each for 15 min;

(2) Step 2: Amino Acid Coupling

Rink MBHA resin is taken as a carrier, 1-hydroxybenzotriazole (3×) and N,N-diisopropyl carbodiimide (3×) as coupling agents, N,N-dimethyl formamide as a solvent, for programmed reaction, and the condensation reaction is carried out successively to connect the protected amino acids, thereby obtaining:

($PEG_2$-$PEG_2$-γGlu(OtBu)-$CO(CH_2)_{18}CO$(OtBu))-Val-Iva-Gly-Ser(tBu)-Pro-Ser(tBu)-Ala-Gln (Trt)-Glu(OtBu)-Glu(OtBu)-Ala-Ser(tBu)-Pro-Ala-Rink Amide MBHA peptide resin, wherein the ratio of the amount of Fmoc protected amino acid to the amount of resin in each condensation reaction is 3:1, the ratio of 1-hydroxybenzotriazole and N, N-diisopropyl carbodiimide to the amount of Fmoc protected amino acid is 1:1, and the deprotection solution is 20% piperidine DMF solution. After coupling, it is shrunk twice with pure methanol for 15 min each time, and vacuum dried to obtain 4.2 g peptide resin.

(3) Step 3: Peptide Cutting and Deprotection 4.2 g Peptide Resin:

($PEG_2$-$PEG_2$-γGlu(OtBu)-$CO(CH_2)_{18}CO$(OtBu))-Val-Iva-Gly-Ser(tBu)-Pro-Ser(tBu)-Ala-Gln (Trt)-Glu(OtBu)-Glu(OtBu)-Ala-Ser(tBu)-Pro-Ala-Rink Amide MBHA peptide resin is added into the round-bottom flask, and 45 ml cutting fluid TFA/TIS/$H_2O$=95/2.5/2.5 (v/v/v) is added under the ice bath condition; after heating, the temperature of the cracking solution is controlled at 25° C., and stirring is kept for 120 minutes. After filtering, the filtrate is slowly poured into ice diethyl ether with stirring, standing for more than 1.0 hour to precipitate completely. The precipitate is centrifuged with the supernate removed, dried with $N_2$, and vacuumed overnight to obtain 1.2 g crude compound 7 with the peptide sequence:

$(PEG_2\text{-}PEG_2\text{-}\gamma Glu\text{-}CO(CH_2)_{18}CO_2H)$-Val-Iva-Gly-Ser-Pro-Ser-Ala-Gln-Glu-Glu-Ala-Ser-Pro-Ala-$NH_2$.

2) Purification and Salt Transfer 1.2 g of crude product obtained in the step 3 is subjected to ultrasonic dissolution with 5.0% acetic acid in 20 ml solution with acetonitrile: $H_2O$=1:1 (volume ratio), and filtered with 0.45 μm teflon membrane after dissolution and clarification to obtained filtered C5 filtrate. The filtrate is purified by twice semi-preparative HPLC on a 20 mm×250 mm packed column of 20 mm reversed phase C18. The column is eluted for 60.0 minutes at 19 mL/min by using 40-60% acetonitrile-0.1% trifluoroacetic acid/$H_2O$ gradient to collect the components containing C5, which are concentrated to remove acetonitrile, and then subjected to salt transfer for freeze-drying. 145 mg product with the HPLC purity of 98.83% is obtained. The separated product is analyzed by LC-MS, and it is found that the m/2 z value of the protonated molecular ion peak is 1050.4, and the theoretical value is 2099.4.

2. Synthesis of a Peptide Compound 22:

The sequence structure is:

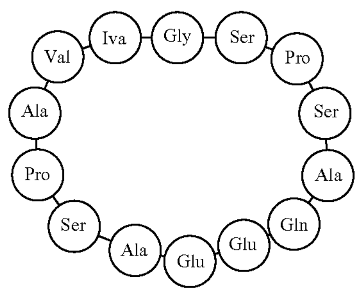 [SMILES: C1CCCCCCCCCCCCC1]

1) Coupling of Main Peptide Chain of Linear Peptide:

The following linear peptide resins with the scale of 0.72 mmol are synthesized on a peptide synthesizer according to Fmoc protection strategy:

Glu(OtBu)-Glu(OtBu)-Ala-Ser((Bu)-Pro-Ala-Val-Iva-Gly-Ser(tBu)-Pro-Ser(tBu)-Ala-γGlu(OAll)-Rink Amide MBHA peptide resin (1) Step 1: Resin Swelling 2 g of Rink amide MBHA resin is swelled in N,N-dimethyl formamide (DMF), and the resin is swelled with N,N-dimethyl formamide for twice, each for 15 min;

(2) Step 2: Amino Acid Coupling

Rink Amide MBHA resin is taken as a carrier, 1-hydroxybenzotriazole (3×) and O-benzotriazole tetramethylurea hexafluorophosphate (3×) as coupling agents, N,N-dimethyl formamide as a solvent, for programmed reaction, and the condensation reaction is carried out successively to connect the protected amino acids, thereby obtaining: Glu(OtBu)-Glu(OtBu)-Ala-Ser(tBu)-Pro-Ala-Val-Iva-Gly-Ser(tBu)-Pro-Ser(tBu)-Ala-γGlu(OAll)-Rink Amide MBHA linear peptide resin, wherein the ratio of the amount of N-Fmoc protected amino acid to the amount of resin in each condensation reaction is 3:1, the ratio of 1-hydroxybenzotriazole and O-benzotriazole tetramethylurea hexafluorophosphate to the amount of N-Fmoc protected amino acid is 3:1, and the deprotection solution is 20% piperidine DMF solution.

(3) Step 3: Removal of OAll Protecting Group

The obtained:

Glu(OtBu)-Glu(OtBu)-Ala-Ser(tBu)-Pro-Ala-Val-Iva-Gly-Ser(tBu)-Pro-Ser(tBu)-Ala-γGlu(OAll)-Rink Amide MBHA peptide resin is dispersed in DMF solution, and 0.15 equivalent tetrakis (triphenylphosphine) platinum and 10 equivalent Morphine are added to react for 12 hours under nitrogen atmosphere, then washed with DCM (10 mL*3) and DMF (10 mL*3) in turn, and pumped dry.

(4) Step 4: cyclization of head and tail amides 1-hydroxybenzotriazole (3×) and O-benzotriazole tetramethylurea hexafluorophosphate (3×) are taken as coupling agents, and N,N-dimethyl formamide is taken as the solvent to react for 4 hours. After coupling, it is shrunk twice with pure methanol for 15 min each time, and vacuum dried to obtain 3.8 g peptide resin after weighing.

(5) Step 5: Polypeptide Cutting and Removal of the Protecting Group 3.8 g resin obtained in (4) is moved to the round-bottom flask, and 40 mL of cutting fluid TFA/TIS/$H_2O$=95/2.5/2.5 (V/V/V) is added under the ice bath condition; after heating, the temperature of the cracking solution is controlled at 25° C., and stirring is kept for 120 minutes. After filtering, the filter cake is washed with a small amount of trifluoroacetic acid for three times, and the filtrates are combined. The filtrate was slowly poured into ice diethyl ether with stirring, placed on standing for more than 2 hours to precipitate completely. standing for more than 1.0 hour to precipitate completely. The precipitate is centrifuged, and washed with ice diethyl ether for three times to obtain precipitate which is dried with $N_2$, and vacuumed overnight to obtain 1.0 g crude compound 22.

2) Purification and Salt Transfer:

1.0 g of crude product obtained in the step 5 is subjected to ultrasonic dissolution with 30 ml pure water, and filtered with 0.45 μm teflon membrane after dissolution to obtain filtered 22 filtrate. The filtrate is purified by twice semi-preparative HPLC on a 20 mm×250 mm packed column of 20 mm reversed phase C18. The column is eluted for 60.0 minutes at 19 mL/min by using 15-35% acetonitrile-0.1% trifluoroacetic acid/$H_2O$ gradient to collect the components containing polypeptide components 22, which are concentrated to remove acetonitrile, and then subjected to salt transfer for freeze-drying. 90 mg product with the HPLC purity of 99.92% is obtained. The separated product is analyzed by LC-MS, and it is found that the m/z+1 value of the protonated molecular ion peak is 1311.25, and the theoretical value is 1309.62.

The peptide compounds synthesized on basis of the above steps areas shown in Table 1 below:

TABLE 1

Peptide Compound of the Present Invention

| Compound No. | | Structure | Molecular weight determination |
|---|---|---|---|
| 1 | SEQ ID NO. 1 | $(PEG_2\text{-}PEG_2\text{-}\gamma Glu\text{-}CO(CH_2)_{18}CO_2H)$-Val-Val-Gly-Ser-Pro-Ser-Ala-Gln-Asp-Glu-Ala-Ser-Pro-Leu-$NH_2$ | 2127.5 |
| 2 | SEQ ID NO. 2 | $(PEG_2\text{-}PEG_2\text{-}\gamma Glu\text{-}CO(CH_2)_{18}CO_2H)$-Val-Val-Gly-Ser-Pro-Ser-Ala-Gln-Asp-Glu-Ala-Ser-Pro-Ala-$NH_2$ | 2085.4 |

TABLE 1-continued

| Peptide Compound of the Present Invention | | | |
|---|---|---|---|
| Compound No. | | Structure | Molecular weight determination |
| 3 | SEQ ID NO. 3 | (PEG$_2$-PEG$_2$-γGlu-CO(CH$_2$)$_{18}$CO$_2$H)-Val-Iva-Gly-Ser-Pro-Ser-Ala-Gln-Asp-Glu-Ala-Ser-Pro-Leu-NH$_2$ | 2127.8 |
| 4 | SEQ ID NO. 4 | (PEG$_2$-PEG$_2$-γGlu-CO(CH$_2$)$_{18}$CO$_2$H)-Val-Val-Gly-Ser-Pro-Ser-Ala-Gln-Glu-Glu-Ala-Ser-Pro-Leu-NH$_2$ | 2141.6 |
| 5 | SEQ ID NO. 5 | (PEG$_2$-PEG$_2$-γGlu-CO(CH$_2$)$_{18}$CO$_2$H)-Val-Iva-Gly-Ser-Pro-Ser-Ala-Gln-Asp-Glu-Ala-Ser-Pro-Ala-NH$_2$ | 2085.8 |
| 6 | SEQ ID NO. 6 | (PEG$_2$-PEG$_2$-γGlu-CO(CH$_2$)$_{18}$CO$_2$H)-Val-Iva-Gly-Ser-Pro-Ser-Ala-Gln-Asp-Glu-Ala-Ser-Pro-Ala | 2086.4 |
| 7 | SEQ ID NO. 7 | (PEG$_2$-PEG$_2$-γGlu-CO(CH$_2$)$_{18}$CO$_2$H)-Val-Iva-Gly-Ser-Pro-Ser-Ala-Gln-Glu-Glu-Ala-Ser-Pro-Ala-NH$_2$ | 2099.4 |
| 8 | SEQ ID NO. 8 | (PEG$_2$-PEG$_2$-γGlu-CO(CH$_2$)$_{18}$CO$_2$H)-Val-Iva-Gly-Ser-Pro-Ser-Ala-Gln-Glu-Glu-Ala-Ser-Pro-Ala | 2100.6 |
| 9 | SEQ ID NO. 9 | (PEG$_2$-PEG$_2$-γGlu-CO(CH$_2$)$_{18}$CO$_2$H)-Val-Iva-Gly-Ser-Pro-Ser-Ala-Gln-Glu-Asp-Ala-Ser-Pro-Ala-NH$_2$ | 2085.4 |
| 10 | SEQ ID NO. 10 | (PEG$_2$-PEG$_2$-γGlu-CO(CH$_2$)$_{18}$CO$_2$H)-Val-Val-Gly-Ser-Pro-Ser-Ala-Gln-Glu-Asp-Ala-Ser-Pro-Ala-NH$_2$ | 2085.8 |
| 11 | SEQ ID NO. 11 | (PEG$_2$-PEG$_2$-γGlu-CO(CH$_2$)$_{18}$CO$_2$H)-Val-Iva-Gly-Ser-Pro-Ser-Ala-Gln-Glu-Glu-Ala-Ser-Pro-Leu-NH$_2$ | 2141.5 |
| 12 | SEQ ID NO. 12 | (PEG$_2$-PEG$_2$-γGlu-CO(CH$_2$)$_{18}$CO$_2$H)-Val-Val-Gly-Ser-Pro-Ser-Ala-Gln-Glu-Asp-Ala-Ser-Pro-Leu-NH$_2$ | 2127.5 |
| 13 | SEQ ID NO. 13 | (PEG$_2$-PEG$_2$-γGlu-CO(CH$_2$)$_{18}$CH$_3$)-Val-Iva-Gly-Ser-Pro-Ser-Ala-Gln-Glu-Glu-Ala-Ser-Pro-Ala-NH$_2$ | 2069.8 |
| 14 | SEQ ID NO. 14 | (PEG$_2$-PEG$_2$-YGlu-CO(CH$_2$)$_{16}$CO$_2$H)-Val-Iva-Gly-Ser-Pro-Ser-Ala-Gln-Glu-Glu-Ala-Ser-Pro-Ala-NH$_2$ | 2071.4 |
| 15 | SEQ ID NO. 15 | (PEG$_2$-PEG$_2$-CO(CH$_2$)$_{18}$CO$_2$H)-Val-Iva-Gly-Ser-Pro-Ser-Ala-Gln-Glu-Glu-Ala-Ser-Pro-Ala-NH$_2$ | 1970.3 |
| 16 | SEQ ID NO. 16 | (PEG$_2$-PEG$_2$-CO(CH$_2$)$_{18}$CO$_2$H)-Val-Iva-Gly-Ser-Pro-Ser-Ala-Gln-Asp-Glu-Ala-Ser-Pro-Ala-NH$_2$ | 1956.6 |
| 17 | SEQ ID NO. 17 | 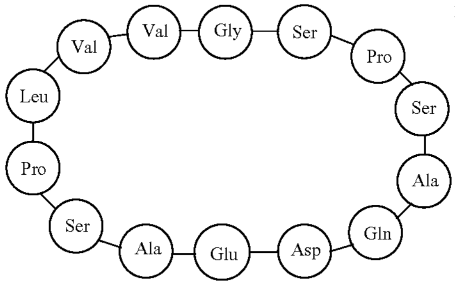 | 1338.5 |
| 18 | SEQ ID NO. 18 | 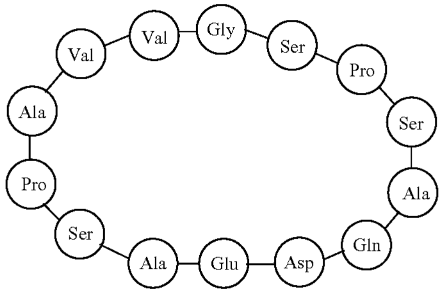 | 1296.4 |

TABLE 1-continued
| Peptide Compound of the Present Invention | | | |
|---|---|---|---|
| Compound No. | | Structure | Molecular weight determination |
| 19 | SEQ ID NO. 19 | 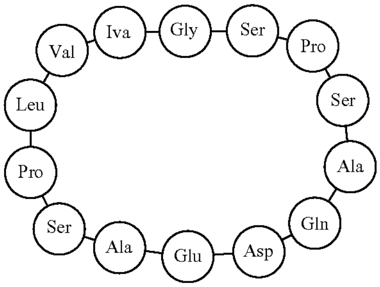 [SMILES: C1CCCCCCCCCCCCC1] | 1338.5 |
| 20 | SEQ ID NO. 20 | 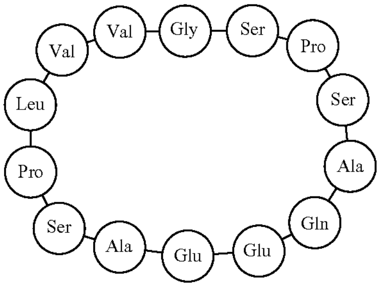 [SMILES: C1CCCCCCCCCCCCC1] | 1352.6 |
| 21 | SEQ ID NO. 21 | 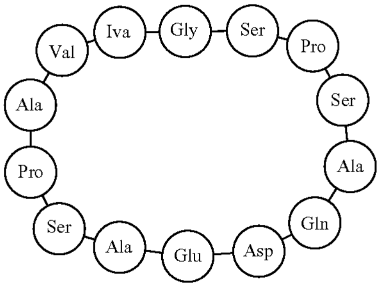 [SMILES: C1CCCCCCCCCCCCC1] | 1296.4 |
| 22 | SEQ ID NO. 22 | 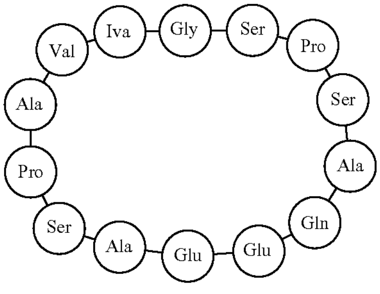 [SMILES: C1CCCCCCCCCCCCC1] | 1311.2 |
| 23 | SEQ ID NO. 23 | 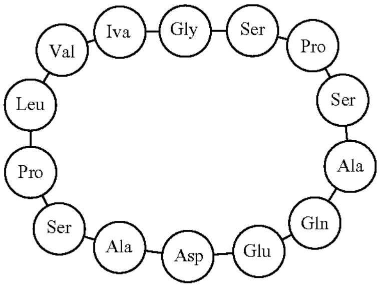 [SMILES: C1CCCCCCCCCCCCC1] | 1338.8 |

TABLE 1-continued

| Peptide Compound of the Present Invention | | | |
|---|---|---|---|
| Compound No. | | Structure | Molecular weight determination |
| 24 | SEQ ID NO. 24 | 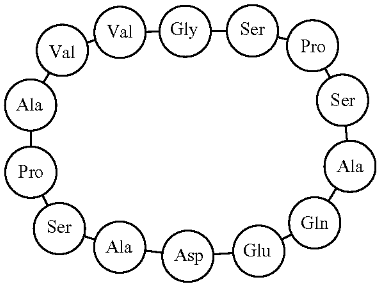 [SMILES: C1CCCCCCCCCCCCC1] | 1296.4 |
| 25 | SEQ ID NO. 25 | 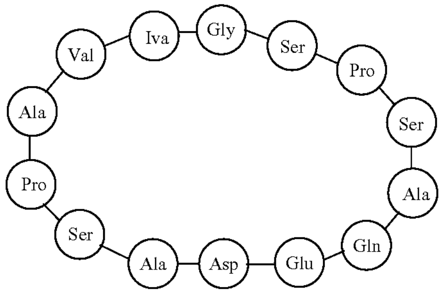 | 1296.6 |

Embodiment 2 Evaluation of Activity of Compounds 1-25 in LX2 Cell Model

In LX2 cell model (which can be directly used as the evaluation model of hepatic fibrosis cells in vitro, because LX2 cells are human liver activated stellate cells. The LX2 cells are purchased from China Center for Type Culture Collection of the Chinese Academy of Sciences, Shanghai, China), the anti-fibrosis activities of peptide compounds1-25arepreliminarily screened, and the expression of the marker α-SMA protein of myofibroblast activation is detected. The peptide compounds1-25 is subjected to cell incubation for 48 hours by using two concentrations (1.0 μM and 10.0 μM). The control group is given the same volume of Dulbecco's modified Eagle medium (DMEM) (purchased from Gibco in the United States), and GAPDH (purchased from TransGen Biotech) as the internal reference. α-actin (α-SMA) is a symbolic feature that distinguishes myoblast cells from myofibroblasts.

The experimental results are as shown in FIG. 1. It is obvious from the statistical graph of the experimental results that, compared with the GAPDH internal reference, the peptide compounds of the present invention have different effects on significantly inhibiting and improving the activity of α-SMA. The peptide compounds 1, 5, 7, 11, 12, 13, 17, 18, 21 and 22 have better effects on inhibiting and improving the activity of α-SMA. The experimental results also show that the peptide compound of the present invention can inhibit the formation of fibrosis at the cellular level, and the results also indicate that the novel peptide compound can potentially be used in the study of organ fibrosis and fibrotic conditions accompanying organ diseases.

Embodiment 3 Pharmacodynamic Evaluation Experiment of Peptide Compounds 1, 5, 7, 11, 12, 13, 17, 18, 21 and 22 on Carbon Tetrachloride ($CCl_4$) Induced Hepatic Fibrosis Mode 1. Test drug: compounds analog. Preservation condition: −20° C..

Molding method: 72 male C57BL/6J mice, male, 18-22 g in weight and 8 weeks old, provided by Laboratory Animal Center, Sun Yat-sen University, randomly divided into 12 groups: 1) control group (Oil)+saline, intraperitoneal injection, n=6; 2) model control group ($CCl_4$)+saline, intraperitoneal injection, n=6; administration of $CCl_4$ to mice once every three days for 6 weeks; 3) model administration group ($CCl_4$)+100.0 μg/kg series of compounds (group 10), intraperitoneal injection, n=6/group. The mice in the control group are injected with corn oil at the same volume and frequency according to the administration volume of 20% $CCl_4$ at the weight of 5.0 μL/g. Administration frequency: administration of $CCl_4$ to mice once every three days for 6 weeks. After 3 weeks of administration of $CCl_4$ to mice in the model administration group, peptide compounds 1, 5, 7, 11, 12, 13, 17, 18, 21 and 22 are administered for 3 weeks from the 4th week. $CCl_4$ and Oil are purchased from Shanghai Aladdin Biochemical Technology Co., Ltd.

2. Pharmacodynamic Evaluation:

In the CCL induced hepatic fibrosis model, the manifestations are: inflammatory cell infiltration around the central vein area, hydropic degeneration of hepatic cells, and increased accumulation of collagen fibers in the portal area and the hepatic interlobular septum. After three weeks of administration, the mice are treated and sampled. Blood is taken from the retrobulbar vein for detection of serological indicators, and liver tissue is taken for pathological analysis.

3. Experimental Methods:

Hematoxylin-eosin (H&E) staining: paraffin embedded tissue sections are taken and baked at 60° C. for 1h. Dewaxing and hydration: xylene for 20 minutes→xylene for 20 minutes→absolute alcohol for 15 minutes→absolute alcohol for 15 minutes→95% alcohol for 10 minutes→90% alcohol for 5 minutes→80% alcohol for 5 minutes. Staining: hematoxylin for 7 minutes→rinsing with tap water→differentiation with 1% hydrochloric acid alcohol for 1s→rinsing with tap water→eosin staining for 15s-20s→rinsing with tap water. Dehydration and transparency: 75% alcohol for 1s→85% alcohol for 1s→95% alcohol for 1s→100% alcohol for 1s→xylene for 1s→xylene for 1s. The sections are aired for 30 minutes and sealed with gum.

Sirius red staining: drying and dewaxing; standing for 5.0 minutes in double distilled water; Sirius red staining for 60-80 minutes in a dark room; washing for 5s with 0.5% glacial acetic acid; dehydration and transparency, sealing and taking photos.

Immunohistochemistry: drying sections, dewaxing, and then soaking in double distilled water for 5 minutes. Antigen retrieval: putting the shelf where pathological sections are placed into a beaker containing citric acid buffer (PH=6.0), and keeping it under high temperature and pressure for 15 minutes; taking out the beaker and letting it stand at room temperature until the temperature drops to the room temperature, then taking out the sections and putting them into 3.0% hydrogen peroxide for 10 minutes to block the endogenous peroxidase activity, and then washing them with PBS for three times, 5 minutes each time; sealing the tissues with 1.0% BSA for 1h; removing 1.0% BSA, adding Collagen I antibody on the tissue according to the proportion recommended in the Description, and staying overnight at 4° C.; taking out the pathological sections next day, adding the second antibody with horseradish peroxidase after the room temperature is restored, incubating it at 37° C. for 60 minutes, and then use DAB (diaminobenzidine) (TH&Ermo Scientific, USA) to develop color; and re-staining with hematoxylin staining solution, washing with tap water for 5 minutes, differentiating with 1% hydrochloric acid alcohol, then washing with tap water for 5 minutes again, dehydrating, airing, sealing, and taking photos (H&E staining solution and Sirius red staining solution are purchased from Sangon Biotech (Shanghai) Co., Ltd., and Collagen I antibody is purchased from CST Corporation).

Figure 2:
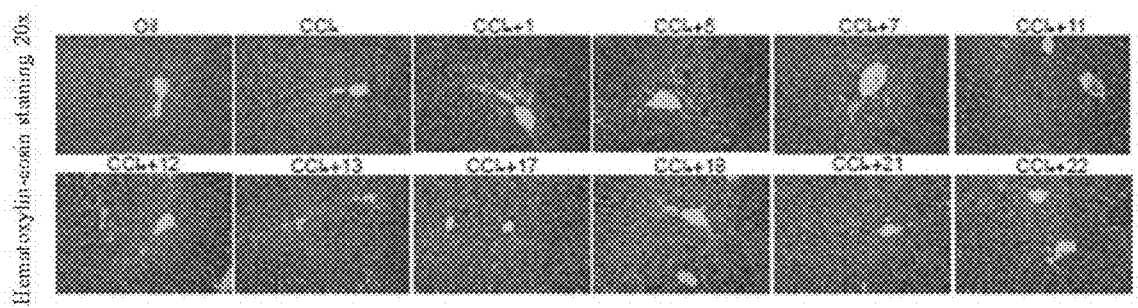
FIG. 2 is an HE staining pathological section of mouse liver in Embodiment 3.
Figure 3:
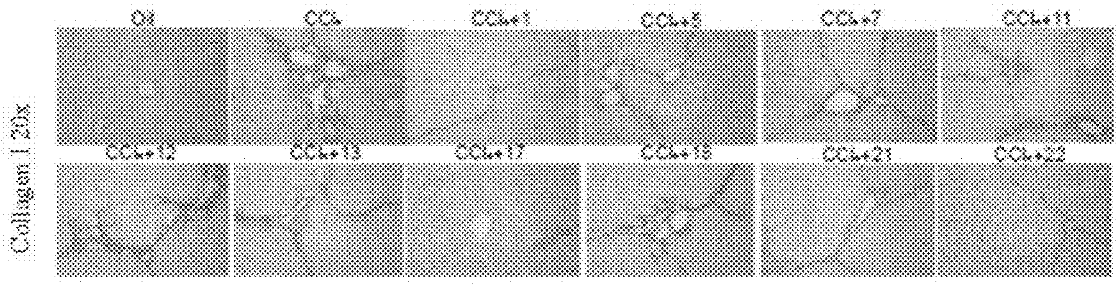
FIG. 3 is a Collagen I immunohistochemical staining pathological section and statistical histogram for mouse liver in Embodiment 3 ( indicates that the confidence level is >99%, and the difference between the two is very significant (P<0.01); * indicates that the confidence level is >99.9%, and the difference between the two is extremely significant (P<0.001).
Figure 3:
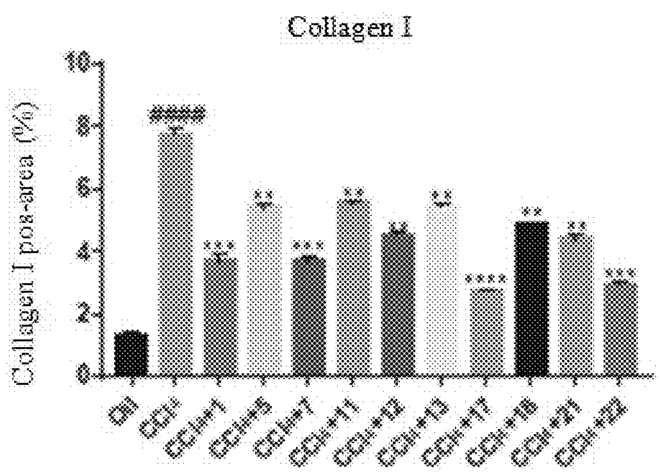
Figure 4:
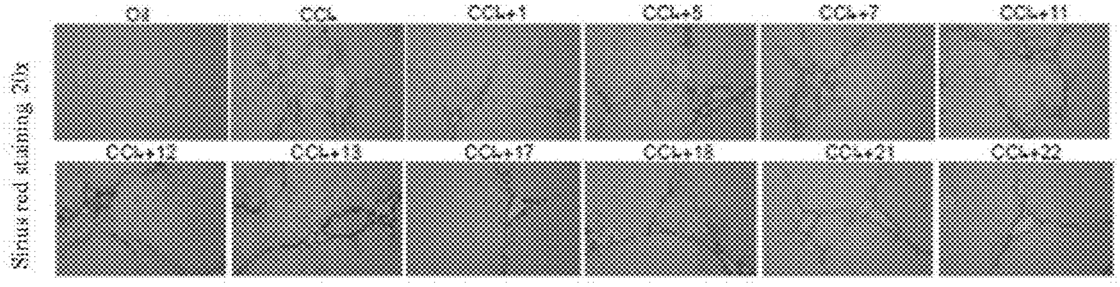
FIG. 4 is the Sirus red staining pathological section and statistical histogram for mouse liver in Embodiment 3 ( indicates that the confidence level is >95%, and the difference between the two is significant (P<0.05);  indicates that the confidence level is >99%, and the difference between the two is very significant (P<0.01); *** indicates that the confidence level is >99.9%, and the difference between the two is extremely significant (P<0.001).
Figure 4:
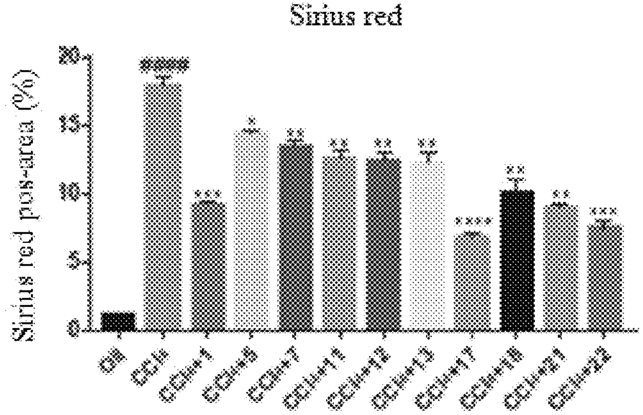

4. Results Analysis:

Referring to FIGS. 2-4, the results show that when the model control group ($CCl_4$)+saline is injected intraperitoneally, $CCl_4$ is administered to mice once every three days for six weeks. Hematoxylin-eosin (H&E) staining, Sirius red staining and Collagen I immunohistochemistry show that the hepatic fibrosis is obvious for the inflammatory cell infiltration in mice liver induced by $CCl_4$.

FIG. 2 shows that: after the model administration group ($CCl_4$)+100.0 μg/kg series of compounds 1, 5, 7, 11, 12, 13, 17, 18, 21 and 22 is treated with the above compounds, the aggregation of inflammatory cells in the liver in each treatment model group is significantly improved; The hepatic fibrosis of mice in each model group is significantly improved after administration of drugs 1, 5, 7, 11, 12, 13, 17, 18, 21 and 22. It indicates that compounds 1, 5, 7, 11, 12, 13, 17, 18, 21 and 22 can inhibit the accumulation of ECM and improve hepatic fibrosis.

FIG. 3 shows that: after the model administration group ($CCl_4$)+100.0 μg/kg series of compounds 1, 5, 7, 11, 12, 13, 17, 18, 21 and 22 is treated with the above compounds, the expression of Collagen I in the liver in each treatment model group shows significant therapeutic improvement.

FIG. 4 shows that: after the model administration group ($CCl_4$)+100.0 μg/kg series of compounds 1, 5, 7, 11, 12, 13, 17, 18, 21 and 22 is treated with the above compounds, the collagen deposition in the liver in each treatment model group shows significant therapeutic improvement.

Embodiment 4 Pharmacodynamic Evaluation of Peptide Compounds 1, 5, 7, 11, 12, 13, 17, 18, 21 and 22 on Bleomycin (BLM) Induced Pulmonary Fibrosis Mode in Mice 1. Test Drug: Compounds Analog. Preservation Condition: −20° C..

Molding method: 78 male C57BL/6J mice, 16-18 g in weight and 6-8 weeks old, provided by Laboratory Animal Center, Sun Yat-sen University, randomly divided into 13 groups: 1) normal control group (Normal), n=6; 2) sham-operated saline control group (Saline), n=6; 3) bleomycin model group (BLM), n=6; and 4) model treatment group: administration of 150 μg/kg series compounds to mice, 10 groups in total, n=6/group. On the 7th day after the operation of bleomycin induced pulmonary fibrosis in mice, mice in the model treatment group are treated with drugs (administration frequency: daily administration/150 μg/kg, intraperitoneal injection). Samples are taken 14 days after administration, and pathological observations are recorded.

2. Pharmacodynamic Evaluation:

The bleomycin (purchased from TCI Shanghai)) induced pulmonary fibrosis model manifests the following pathological features: bronchiectasis, hydropic degeneration of bronchial epithelial cells, obvious edema and widening of alveolar interstitium, and deposition of a large number of fibroblasts and collagen tissue. The alveolar structure almost completely disappears, filled with fibrous connective tissue, and accompanied by inflammatory cell infiltration. After 14 days of administration, the mice in the model treatment group are treated and sampled. Blood is taken from the retrobulbar vein for detection of serological indicators, and liver tissue is taken for pathological analysis.

3. Experimental Methods:

H&E staining: paraffin embedded tissue sections are taken and baked at 60° C. for 1h. Dewaxing and hydration: xylene for 20 minutes→xylene for 20 minutes→absolute alcohol for 15 minutes→absolute alcohol for 15 minutes→95% alcohol for 10 minutes→90% alcohol for 5 minutes→80% alcohol for 5 minutes. Staining: hematoxylin for 7 minutes→rinsing with tap water→differentiation with 1% hydrochloric acid alcohol for 1s→rinsing with tap water→eosin staining for 15s-20s→rinsing with tap water. Dehydration and transparency: 75% alcohol for 1s→85% alcohol for 1s→95% alcohol for 1s→100% alcohol for 1s→xylene for 1s→xylene for 1s. The sections are aired for 30 minutes and sealed with gum.

Masson staining: drying and dewaxing; mordanting; adding celestine blue staining solution for 2-3 min, and washing with water; adding Mayer hematoxylin staining solution and washing with water; differentiating with acid alcohol differentiation liquid for several seconds, and washing with tap water; adding ponceau magenta staining solution and washing with distilled water; treating with phosphomolybdic acid solution; adding aniline blue staining solution for 5 min; treating with weak acid solution for 2 min; dehydration and transparency, airing and sealing with gum.

Immunohistochemistry: drying sections, dewaxing, and then soaking in double distilled water for 5 minutes. Antigen retrieval: putting the shelf where pathological sections are placed into a beaker containing citric acid buffer (PH=6.0), and keeping it under high temperature and pressure for 15 minutes; taking out the beaker and letting it stand at room temperature until the temperature drops to the room temperature, then taking out the sections and putting them into 3.0% hydrogen peroxide for 10 minutes to block the endogenous peroxidase activity, and then washing them with PBS for three times, 5 minutes each time; sealing the tissues with 1.0% BSA for 1h; removing 1.0% BSA, adding Collagen I antibody on the tissue according to the proportion recommended in the Description, and staying overnight at 4° C.; taking out the pathological sections next day, adding the second antibody with horseradish peroxidase after the room temperature is restored, incubating it at 37° C. for 60 minutes, and then use DAB (diaminobenzidine) (TH&Ermo Scientific, USA) to develop color; and re-staining with hematoxylin staining solution, washing with tap water for 5 minutes, differentiating with 1% hydrochloric acid alcohol, then washing with tap water for 5 minutes again, dehydrating, airing, sealing, and taking photos (H&E staining solution and Sirius red staining solution are purchased from Sangon Biotech (Shanghai) Co., Ltd., and Collagen I antibody is purchased from CST Corporation).

Figure 5:
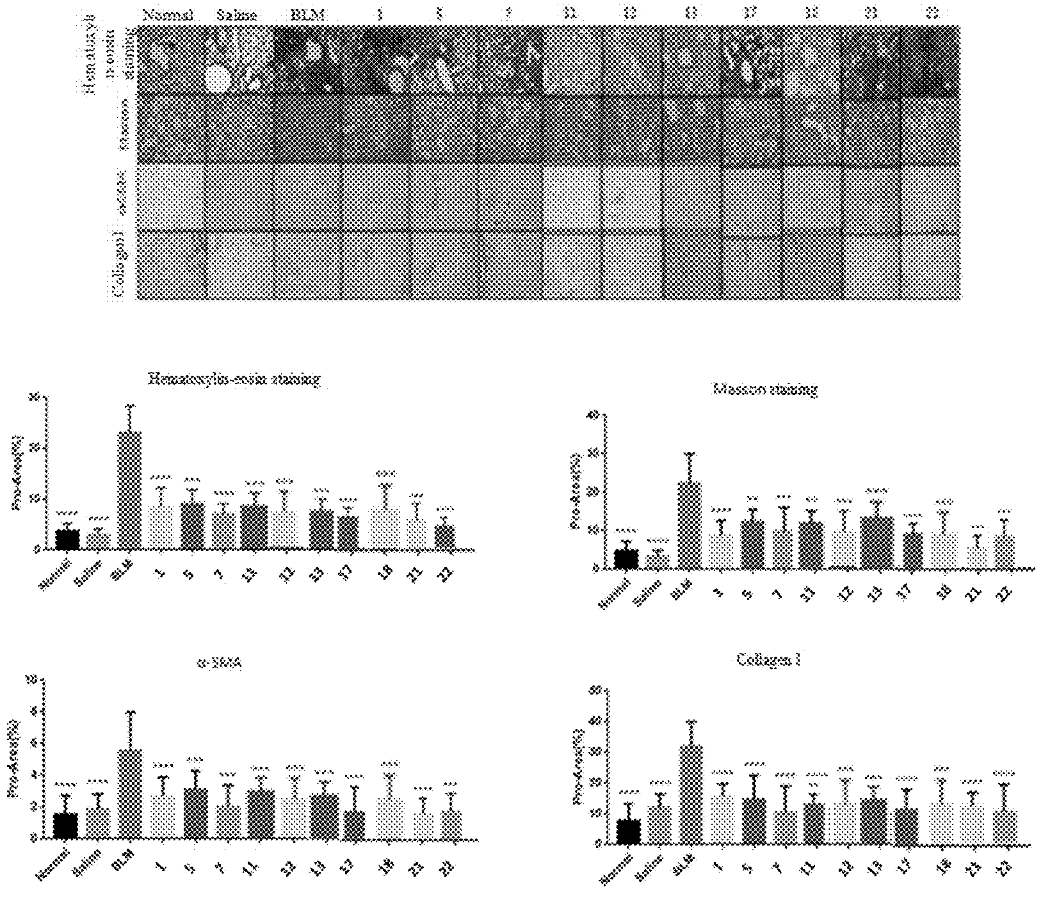
FIG. 5 is an HE staining, Masson staining, α-SMA and Collagen1 immunohistochemical pathological section and statistical histogram for mouse liver in Embodiment 4 ( indicates that the confidence level is >99%, and the difference between the two is very significant (P<0.01); * indicates that the confidence level is >99.9%, and the difference between the two is extremely significant (P<0.001); * indicates that the confidence level is >99.99%, and the difference between the two is extremely significant (P<0.0001).

4. Results Analysis:

Referring to FIG. 5, the results show that: H&E staining: the lung tissue structure of the normal control group and sham operated saline control group is clear, no thickening of alveolar wall, complete alveolar epithelium structure, and no inflammatory cell infiltration. Masson staining: Only a few collagen fibers are stained blue in the normal control group and the sham operated saline control group. Compared with bleomycin model group, the mice in the model treatment group are treated with 150.0 μg/kg series compounds 1, 5, 7, 11, 12, 13, 17, 18, 21 and 22, the pulmonary fibrosis of mice in each treatment model group shows significant therapeutic improvement. After 14 days of administration, H&E staining and Masson staining show that the alveolar septa in bleomycin group are significantly widened, and a large number of fibroblasts and matrix filling are observed; the degree of pulmonary fibrosis in each treatment group is significantly reduced compared with that in the bleomycin control group after treatment with compounds 1, 5, 7, 11, 12, 13, 17, 18, 21 and 22.

α-SMA and Collagen1 immunohistochemistry show that the alveolar septa in bleomycin group are significantly widened, and a large amount of yellow stained fibronectin is filled in the pulmonary parenchyma; the fibronectin in pulmonary parenchyma is significantly less than that in bleomycin group after treatment with compounds 1, 5, 7, 11, 12, 13, 17, 18, 21 and 22. It indicates that the expression of lung tissue α-SMA, Collagen 1 is significantly inhibited after administration. The above results indicate that compounds 1, 5, 7, 11, 12, 13, 17, 18, 21 and 22 can significantly treat and improve pulmonary fibrosis.

Figure 6:
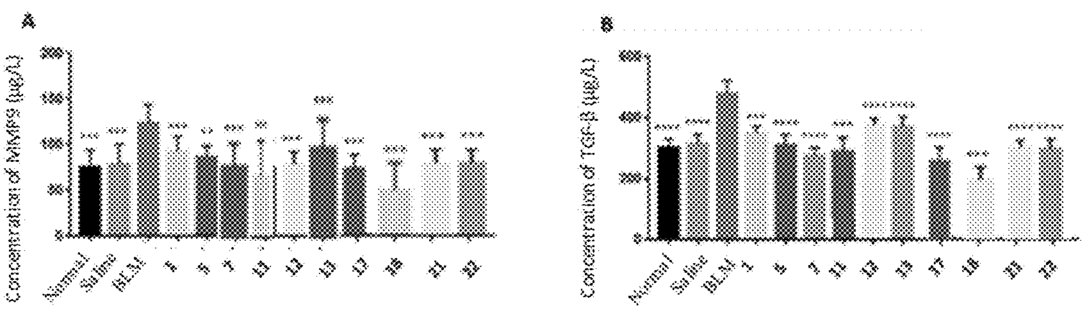
FIG. 6 is a statistical histogram for the expression of TGFβ and MMP9 cell factors in each group of mouse serum detected by ELISA in Embodiment 4 ( indicates that the confidence level is >99%, and the difference between the two is very significant (P<0.01); * indicates that the confidence level is >99.9%, and the difference between the two is extremely significant (P<0.001); * **** indicates that the confidence level is >99.99%, and the difference between the two is extremely significant (P<0.0001).
Figure 7:
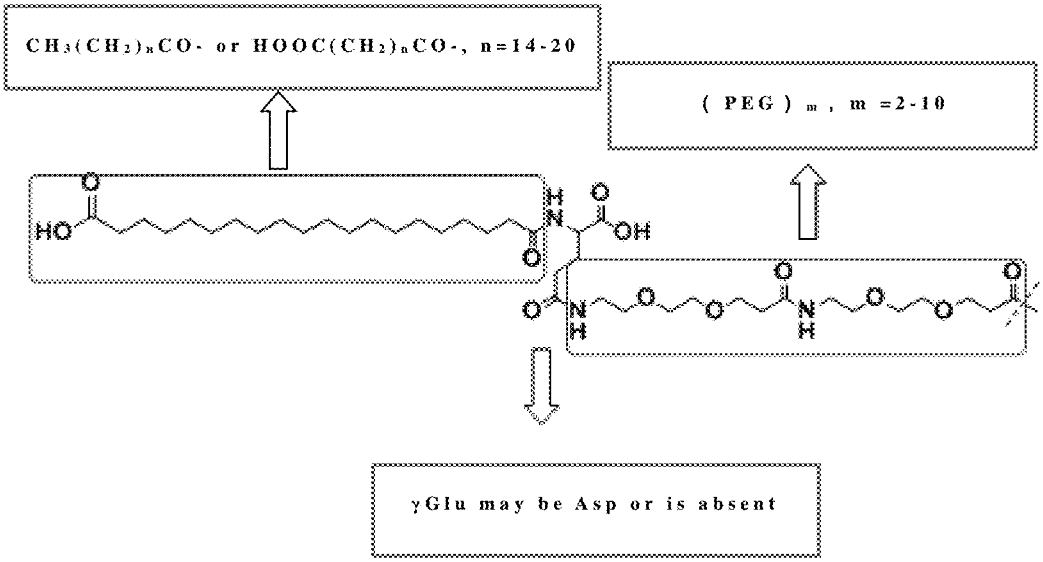
FIG. 7 is a schematic diagram of the connection between the bridging group and the peptide chain in the compound of the present invention.

The occurrence and development of fibrotic diseases are related to TGF-β and MMP-9 induced EMT process. Matrix metalloproteinases (MMPs) are matrix degrading proteases that degrade all components of extracellular matrix. They participate in the pathophysiological process of pulmonary fibrosis, play an important role in the abnormal remodeling of extracellular matrix and destruction of basement membrane, and promote the recruitment of inflammatory cells and fibroblasts. The increased expression of MMP-9 in pulmonary fibrosis animal models and patients, higher than the normal MMP-9 level, may destroy normal tissue structure and increase the migration of inflammatory cells to the disease site. In order to further explore the inhibitory mechanism of polypeptide drugs on bleomycin induced pulmonary fibrosis, we detect the expression of TGFβ, MMP9 cell factors in serum of mice in each group by ELISA. Referring to FIG. 6-A, compared with the normal control group and the sham operated saline control group, the pulmonary MMP-9 in the bleomycin model group increases significantly; Administration of compounds 1, 5, 7, 11, 12, 13, 17, 18, 21 and 22 can significantly reduce the concentration of MMP9 in serum of mice, which may be related to the degree of the pulmonary fibrosis. We speculate that its mechanism should be related to TGF-β. Referring to FIG. 6-B, the results of ELISA show that compounds 1, 5, 7, 11, 12, 13, 17, 18, 21 and 22 can significantly reduce the concentration of TGF-β in serum of mice.

According to the above experimental results, the polypeptide compound of the present invention inhibits the accumulation of ECM and the expression of lung tissue α-SMA, Collagen 1, and it can be used for treating hepatic fibrosis and fibrotic conditions accompanying hepatic disease as well as idiopathic pulmonary fibrosis and fibrotic conditions accompanying pulmonary disease.

What is claimed is:

1. A peptide compound targeting elastin-derived peptides comprising a parent peptide represented by the following amino acid sequence:

$R_1$-Val-Xa2-Gly-Ser-Pro-Ser-Ala-Gln-Xa9-Xa10-Ala-Ser-Pro-Xa14, wherein, $R_1$ is a lipophilic substituent or is absent;

Xa2=Val or Iva;

Xa9=Asp or Glu;

Xa10=Glu or Asp;

Xa14=Ala.

2. The peptide compound according to claim 1, wherein an amino group of Val at position 1 is attached to a lipophilic substituent via a bridging group; the bridging group comprises $(PEG)_m$, $(PEG)_m$ and γGlu, or $(PEG)_m$ and Asp, and wherein the amino group of Val at position 1 is attached to the lipophilic substituent via PEGylation of $(PEG)_m$ in the bridging group; the lipophilic substituent is $CH_3(CH_2)_nC(O)$— or $HOOC(CH_2)_nC(O)$—, and an acyl thereof and an amino in the bridging group form an amido bond; wherein m is an integer of 2 to 10, and n is an integer of 14-20; and wherein a carboxyl terminal of the amino acid sequence is a bare carboxyl group or is attached to an amino group to form a —$CONH_2$ group.

3. The peptide compound according to claim 1, wherein an amino group of Val at position 1 and a carboxyl group of the amino acid at position 14 in the amino acid sequence form an amido bond to make up a cyclic peptide compound when $R_1$ is absent; wherein the cyclic peptide compound is represented as follows:

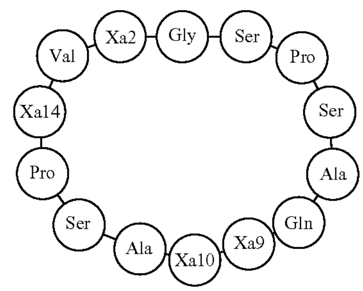 [SMILES: C1CCCCCCCCCCCCC1]

Xa2=Val or Iva;

Xa9=Asp or Glu;

Xa10=Glu or Asp;

Xa14=Ala.

4. The peptide compound according to claim 1, wherein the amino acid sequence of the parent peptide is selected from SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 14, SEQ ID NO: 15, SEQ ID NO: 16, SEQ ID NO: 18, SEQ ID NO: 21, SEQ ID NO: 22, SEQ ID NO: 24 and SEQ ID NO: 25.

5. The peptide compound according to claim 2, wherein a structure linked to the amino group of Val at position 1 in the amino acid sequence of the parent peptide is:

—$(PEG_2$—$(PEG_2$—γGlu—$CO(CH_2)_{18}CO_2H)$;

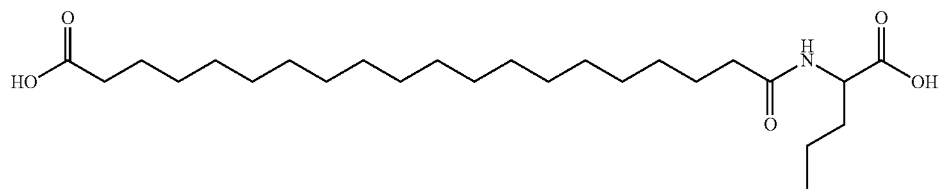

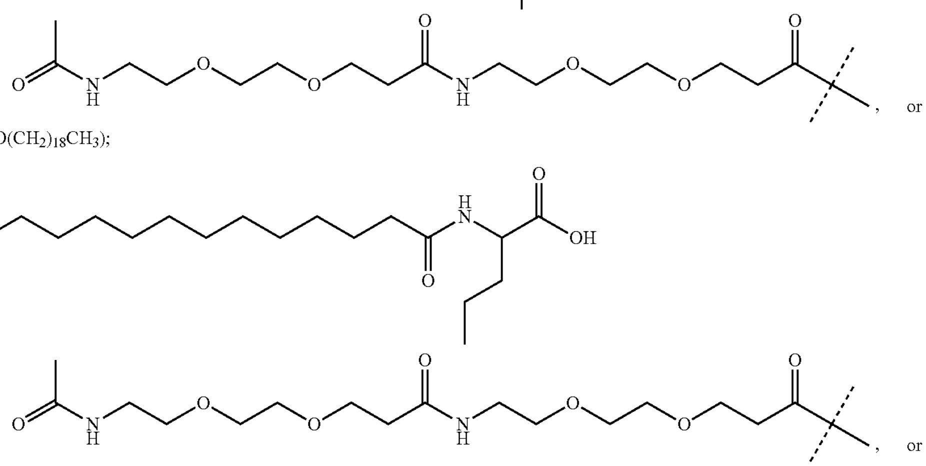

, or

—$(PEG_2$—$(PEG_2$—γGlu—$CO(CH_2)_{18}CH_3)$;

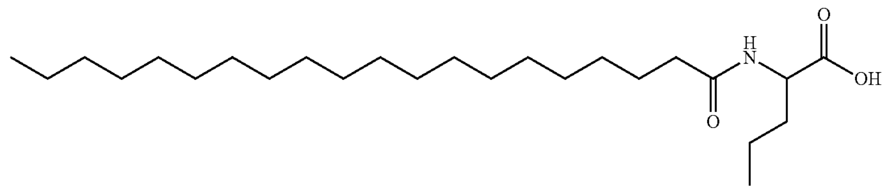

, or

—$(PEG_2$—$(PEG_2$—γGlu—$CO(CH_2)_{16}CO_2H)$;

-continued

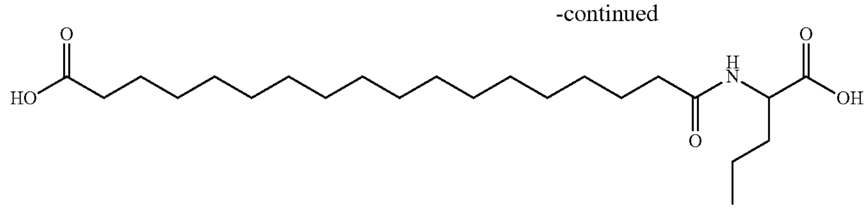

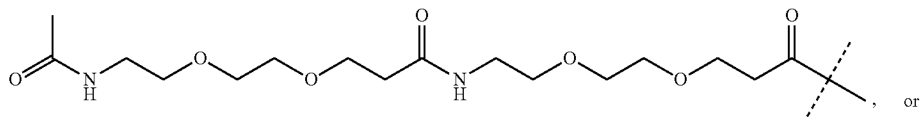

, or

——$(PEG_2—(PEG_2—CO(CH_2)_{18}CO_2H)$;

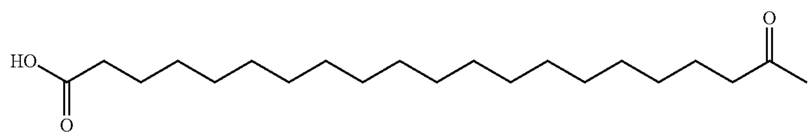

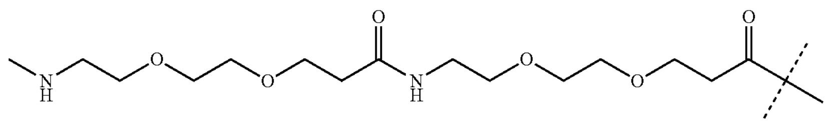

.

6. The peptide compound according to claim 1, wherein the peptide compound is any of the following compounds 2, 5-10, 13-16, 18, 21, 22, 24 and 25:

Compound 2 (SEQ ID NO: 2):
$(PEG_2-PEG_2-\gamma Glu-CO(CH_2)_{18}CO_2H)$-Val-Val-Gly-Ser-Pro-Ser-Ala-Gln-Asp-Glu-Ala-Ser-Pro-Ala-$NH_2$
$(PEG_2-PEG_2-\gamma Glu-CO(CH_2)_{18}CO_2H)$-Val-Val-Gly-Ser-Pro-Ser-Ala-Gln-Glu-Glu-Ala-Ser-Pro-Leu-$NH_2$
Compound 5 (SEQ ID NO: 5):
$(PEG_2-PEG_2-\gamma Glu-CO(CH_2)_{18}CO_2H)$-Val-Iva-Gly-Ser-Pro-Ser-Ala-Gln-Asp-Glu-Ala-Ser-Pro-Ala-$NH_2$
Compound 6 (SEQ ID NO: 6):
$(PEG_2-PEG_2-\gamma Glu-CO(CH_2)_{18}CO_2H)$-Val-Iva-Gly-Ser-Pro-Ser-Ala-Gln-Asp-Glu-Ala-Ser-Pro-Ala
Compound 7 (SEQ ID NO: 7):
$(PEG_2-PEG_2-\gamma Glu-CO(CH_2)_{18}CO_2H)$-Val-Iva-Gly-Ser-Pro-Ser-Ala-Gln-Glu-Glu-Ala-Ser-Pro-Ala-$NH_2$
Compound 8 (SEQ ID NO: 8):
$(PEG_2-PEG_2-\gamma Glu-CO(CH_2)_{18}CO_2H)$-Val-Iva-Gly-Ser-Pro-Ser-Ala-Gln-Glu-Glu-Ala-Ser-Pro-Ala
Compound 9 (SEQ ID NO: 9):
$(PEG_2-PEG_2-\gamma Glu-CO(CH_2)_{18}CO_2H)$-Val-Iva-Gly-Ser-Pro-Ser-Ala-Gln-Glu-Asp-Ala-Ser-Pro-Ala-$NH_2$
Compound 10 (SEQ ID NO: 10):
$(PEG_2-PEG_2-\gamma Glu-CO(CH_2)_{18}CO_2H)$-Val-Val-Gly-Ser-Pro-Ser-Ala-Gln-Glu-Asp-Ala-Ser-Pro-Ala-$NH_2$
Compound 13 (SEQ ID NO: 13):
$(PEG_2-PEG_2-\gamma Glu-CO(CH_2)_{18}CH3)$-Val-Iva-Gly-Ser-Pro-Ser-Ala-Gln-Glu-Glu-Ala-Ser-Pro-Ala-$NH_2$
Compound 14 (SEQ ID NO: 14):
$(PEG_2-PEG_2-\gamma Glu-CO(CH_2)_{16}CO_2H)$-Val-Iva-Gly-Ser-Pro-Ser-Ala-Gln-Glu-Glu-Ala-Ser-Pro-Ala-$NH_2$
Compound 15 (SEQ ID NO: 15):
$(PEG_2-PEG_2-CO(CH_2)_{18}CO_2H)$-Val-Iva-Gly-Ser-Pro-Ser-Ala-Gln-Glu-Glu-Ala-Ser-Pro-Ala-$NH_2$
Compound 16 (SEQ ID NO: 16):
$(PEG_2-PEG_2-CO(CH_2)_{18}CO_2H)$-Val-Iva-Gly-Ser-Pro-Ser-Ala-Gln-Asp-Glu-Ala-Ser-Pro-Ala-$NH_2$
Compound 18 (SEQ ID NO: 18):

-continued

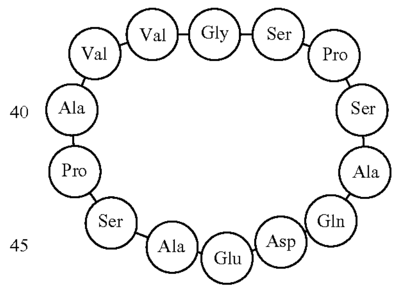

Compound 21 (SEQ ID NO: 21):

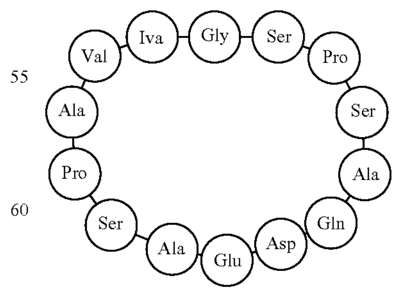

Compound 22 (SEQ ID NO: 22):

-continued

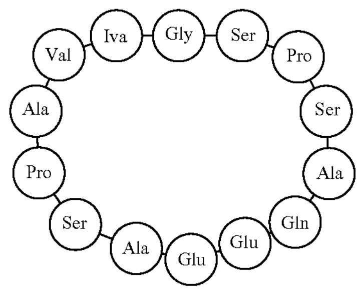 [SMILES: C1CCCCCCCCCCCCC1]

Compound 24 (SEQ ID NO: 24):

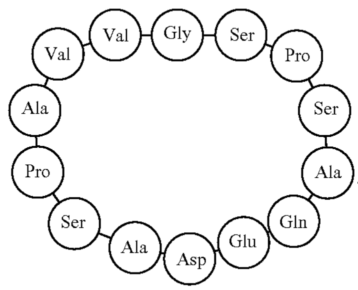

-continued

Compound 25 (SEQ ID NO: 25):

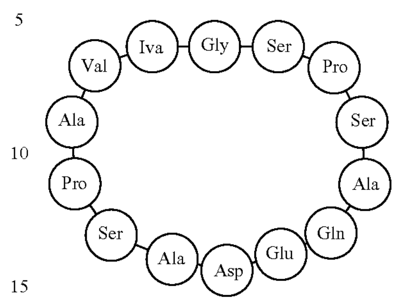

7. A composition comprising the peptide compound according to claim 1.

8. The composition according to claim 7, wherein the composition is a pharmaceutical composition, further comprise a pharmaceutically acceptable carrier or excipients.

9. A method of treating idiopathic pulmonary fibrosis or hepatic fibrosis; wherein the method comprises administering the peptide compound of claim 1 to a subject.

* * * * *